(12) United States Patent
Coffey et al.

(10) Patent No.: US 9,865,096 B2
(45) Date of Patent: Jan. 9, 2018

(54) MATERIAL ANALYSIS OF ANATOMICAL ITEMS

(71) Applicants: Boston Scientific Scimed, Inc., Maple Grove, MN (US); Regents of the University of Minnesota, Minneapolis, MN (US)

(72) Inventors: Dane Coffey, Burbank, CA (US); Daniel F. Keefe, St. Paul, MN (US); Arthur G. Erdman, New Brighton, MN (US); Benjamin J. Bidne, Hanover, MN (US); Gregory Ernest Ostenson, St. Paul, MN (US); David M. Flynn, Lino Lakes, MN (US); Kenneth Matthew Merdan, Loretto, MN (US); Chi-Lun Lin, Minneapolis, MN (US)

(73) Assignees: Boston Scientific Scimed, Inc., Maple Grove, MN (US); Regents of the University of Minnesota, Minneapolis, MN (US)

( * ) Notice: Subject to any disclaimer, the term of this patent is extended or adjusted under 35 U.S.C. 154(b) by 88 days.

(21) Appl. No.: 14/459,163

(22) Filed: Aug. 13, 2014

(65) Prior Publication Data
US 2015/0049082 A1 Feb. 19, 2015

Related U.S. Application Data

(60) Provisional application No. 61/865,596, filed on Aug. 13, 2013, provisional application No. 61/865,407, filed on Aug. 13, 2013.

(51) Int. Cl.
*G06T 17/00* (2006.01)
*G06T 13/20* (2011.01)
(Continued)

(52) U.S. Cl.
CPC ............. *G06T 19/20* (2013.01); *A61B 34/10* (2016.02); *G06K 9/4604* (2013.01);
(Continued)

(58) Field of Classification Search
CPC A61B 2017/00243; A61B 2017/00778; A61B 2034/102; A61B 2034/104;
(Continued)

(56) References Cited

U.S. PATENT DOCUMENTS 5,494,042 A * 2/1996 Panescu ............... A61B 5/0422
600/374
6,608,628 B1 8/2003 Ross et al.
(Continued)

FOREIGN PATENT DOCUMENTS

| DE | 10 2007 028065 | 1/2009 |
| EP | 2765776 | 8/2014 |
| WO | 2015023787 | 2/2015 |

OTHER PUBLICATIONS

International Search Report and Written Opinion in International Application No. PCT/US2014/050944, dated Jan. 15, 2015, 19 pages.
(Continued)

*Primary Examiner* — Sing-Wai Wu
(74) *Attorney, Agent, or Firm* — Pauly, DeVries Smith & Deffner LLC

(57) ABSTRACT

A computer-implemented method for medical device modeling includes accessing an electronic definition for a model of a three-dimensional item and an electronic definition of a three-dimensional spline relating to an internal anatomical volume; determining, with a computer-based finite element analysis system and using the electronic definitions, stresses created by the three-dimensional item along the three-dimensional spline, for different points along the three-
(Continued)

dimensional spline; and displaying stress data generated by the finite element analysis system with a visualization system, the display of the stress data indicating levels of stress on portions of the three-dimensional item at particular locations along the three-dimensional spline.

25 Claims, 23 Drawing Sheets

(51) Int. Cl.

| | |
|---|---|
| G06T 19/20 | (2011.01) |
| G06K 9/46 | (2006.01) |
| G06T 7/00 | (2017.01) |
| G06T 15/00 | (2011.01) |
| G06T 19/00 | (2011.01) |
| G06F 3/01 | (2006.01) |
| A61B 17/00 | (2006.01) |
| A61B 34/10 | (2016.01) |
| A61B 34/20 | (2016.01) |
| A61B 90/00 | (2016.01) |

(52) U.S. Cl.
CPC ........... *G06T 7/0012* (2013.01); *G06T 13/20* (2013.01); *G06T 15/00* (2013.01); *G06T 17/00* (2013.01); *G06T 19/006* (2013.01); *A61B 2017/00243* (2013.01); *A61B 2017/00778* (2013.01); *A61B 2034/102* (2016.02); *A61B 2034/104* (2016.02); *A61B 2034/105* (2016.02); *A61B 2034/107* (2016.02); *A61B 2034/2055* (2016.02); *A61B 2090/368* (2016.02); *G06F 3/01* (2013.01); *G06F 3/011* (2013.01); *G06K 2009/4666* (2013.01); *G06T 2207/10076* (2013.01); *G06T 2207/30004* (2013.01); *G06T 2207/30048* (2013.01); *G06T 2207/30101* (2013.01); *G06T 2211/40* (2013.01); *G06T 2219/00* (2013.01)

(58) Field of Classification Search
CPC ...... A61B 2034/2055; A61B 2090/368; G06K 9/4604; G06T 13/20; G06T 15/00; G06T 17/00; G06T 19/20; G06T 2207/10076; G06T 2207/30004; G06T 2207/30048; G06T 2207/30101; G06T 2211/40; G06T 2219/00
See application file for complete search history.

(56) References Cited

U.S. PATENT DOCUMENTS

| | | | | |
|---|---|---|---|---|
| 7,291,166 | B2* | 11/2007 | Cheng | A61F 2/91 623/1.15 |
| 7,840,393 | B1* | 11/2010 | Whirley | G09B 23/28 703/11 |
| 8,363,096 | B1 | 1/2013 | Aguirre | |
| 8,958,615 | B2 | 2/2015 | Blum et al. | |
| 9,333,361 | B2 | 5/2016 | Zottola et al. | |
| 9,364,665 | B2 | 6/2016 | Chen et al. | |
| 9,411,935 | B2 | 8/2016 | Moffitt et al. | |
| 2003/0212321 | A1 | 11/2003 | Baxter, III et al. | |
| 2003/0216710 | A1* | 11/2003 | Hurt | A61M 25/007 604/523 |
| 2004/0049115 | A1 | 3/2004 | Murphy et al. | |
| 2004/0097805 | A1 | 5/2004 | Verard et al. | |
| 2004/0257361 | A1 | 12/2004 | David Tabakman et al. | |
| 2006/0100502 | A1* | 5/2006 | Chen | A61B 5/02007 600/419 |
| 2006/0290695 | A1 | 12/2006 | Salomie et al. | |
| 2007/0092864 | A1 | 4/2007 | Reinhardt | |
| 2007/0127791 | A1* | 6/2007 | Ernvik | G06F 19/3437 382/128 |
| 2007/0185485 | A1* | 8/2007 | Hauck | A61B 5/6885 606/41 |
| 2008/0137926 | A1 | 6/2008 | Skinner et al. | |
| 2009/0062642 | A1 | 3/2009 | Hauck et al. | |
| 2009/0287186 | A1 | 11/2009 | Adams et al. | |
| 2010/0067768 | A1 | 3/2010 | Ionasec et al. | |
| 2010/0094370 | A1* | 4/2010 | Levin | A61N 1/36564 607/19 |
| 2010/0106475 | A1 | 4/2010 | Smith et al. | |
| 2010/0290679 | A1* | 11/2010 | Gasser | G06T 7/00 382/128 |
| 2010/0318326 | A1 | 12/2010 | Yamamoto et al. | |
| 2011/0170752 | A1 | 7/2011 | Martin et al. | |
| 2012/0296392 | A1 | 11/2012 | Lee et al. | |
| 2013/0172732 | A1 | 7/2013 | Kiraly et al. | |
| 2013/0296845 | A1 | 11/2013 | Bar-Tal et al. | |
| 2014/0225887 | A1 | 8/2014 | Aguirre | |
| 2015/0049081 | A1 | 2/2015 | Coffee et al. | |
| 2015/0049083 | A1 | 2/2015 | Bidne et al. | |
| 2015/0134031 | A1 | 5/2015 | Moffitt et al. | |
| 2016/0151634 | A1 | 6/2016 | Carcieri et al. | |
| 2016/0225152 | A1 | 8/2016 | Blum et al. | |

OTHER PUBLICATIONS

Carvalho et al., "Estimating 3D lumen centerlines of carotid arteries in free-hand acquisition ultrasound," International Journal of Computer Assisted Radiology and Surgery; 7(2), Jun. 29, 2011, pp. 207-215.
Coffey et al., "Interactive Slice WIM: Navigating and Interrogating Volume Datasets Using a Multi-Surface, Multi-Touch VR Interface," Visualization and Computer Graphics, IEEE Transactions on, vol. 18, pp. 1614-1626, 2012.
Coffey et al., "Low Cost VR Meets Low Cost Multi-Touch," Proceedings of the International Symposium on Visual Computing, Springer Lecture Notes in Computer Science, vol. 6454, pp. 351-360, 2010.
Coffey et al., "Slice WIM: a multi-surface, multi-touch interface for overview+detail exploration of volume datasets in virtual reality," presented at the Symposium on Interactive 3D Graphics and Games, San Francisco, California, 2011.
Erdman et al., "Grand Challenge: Applying Regulatory Science and Big Data to Improve Medical Device Innovation," IEEE Transactions on Biomedical Engineering, 60(3), pp. 700-706, 2013.
"Communication Pursuant to Rules 161(1) and 162 EPC," for European Patent Application No. 14758043.5 dated Apr. 13, 2016 (2 pages).
"Non-Final Office Action," for co-owned, co-pending U.S. Appl. No. 14/459,129 dated Mar. 9, 2016 (55 pages).
"Non-Final Office Action," for co-owned, co-pending U.S. Appl. No. 14/459,202 dated Mar. 7, 2016 (49 pages).
"Final Office Action," for U.S. Appl. No. 14/459,129 dated Oct. 11, 2016 (57 pages).
"Response to Final Office Action," for U.S. Appl. No. 14/459,129 filed Dec. 6, 2016 (16 pages).
"Final Office Action," for U.S. Appl. No. 14/459,202 dated Oct. 21, 2016 (52 pages).
"International Preliminary Report on Patentability," for International application No. PCT/US2014/050944 dated Feb. 16, 2016 (12 pages).
"Response to Communication Pursuant to Rules 161(1) and 162 EPC," for European Patent Application No. 14758043.5 filed with the EPO Oct. 24, 2016 (27 pages).
"Non-Final Office Action," for U.S. Appl. No. 14/459,129 dated Feb. 10, 2017 (61 pages).
"Non-Final Office Action," for U.S. Appl. No. 14/459,202, dated Feb. 24, 2017 (56 pages).
"Response to Advisory Action," for U.S. Appl. No. 14/459,129, filed Jan. 11, 2017, (18 pages).
"Response to Final Office Action," for U.S. Appl. No. 14/459,129, filed Dec. 6, 2016, (16 pages).

(56) References Cited

OTHER PUBLICATIONS

"Response to Final Office Action," for U.S. Appl. No. 14/459,202, filed Dec. 20, 2016 (15 pages).
"Response to Non-Final Office Action," for U.S. Appl. No. 14/459,129, filed Aug. 9, 2016 (26 pages).
"Response to Non-Final Office Action," for U.S. Appl. No. 14/459,202, filed Aug. 5, 2016 (26 pages).
"3D Medical Animation Demo—Cardiac Catheterization," Published on Aug. 3, 2012. <https://www.youtube.com/watch?v=hXdNY97Xkmw>.
"Kinect Sensor Allows Surgeons to Manipulate 3D CT Images in Midair," Published Feb. 11, 2011. <https://www.youtube.com/watch?v=id7OZAbFaVI>.
"Non-Final Office Action," for U.S. Appl. No. 14/459,202 dated Jul. 6, 2017 (56 pages).
"Notice of Allowance," for U.S. Appl. No. 14/459,129 dated Jun. 21, 2017 (10 pages).
"Response to Non Final Office Action," for U.S. Appl. No. 14/459,129, filed Apr. 7, 2017, 15 pages.
"Response to Non Final Office Action," for U.S. Appl. No. 14/459,202, filed Aug. 2, 2017, 14 pages.
"Response to Non-Final Office Action," for U.S. Appl. No. 14/459,202, filed Apr. 21, 2017, 14 pages.
"Final Office Action," for U.S. Appl. No. 14/459,202 dated Aug. 24, 2017 (33 pages).
"Video: Cardiology Medical Animation—Deployment of Mitral Valve Clip," Published on Jun. 26, 2009, scientificanim777. URL<https://www.youtube.com/watch?v=yET7if-tLtM> (15 pages).
"Response to Final Office Action", for U.S. Appl. No. 14/459,202, filed Sep. 22, 2017, 14 pages.

* cited by examiner

Load / Configure Image Stack      Load / Apply Meshes

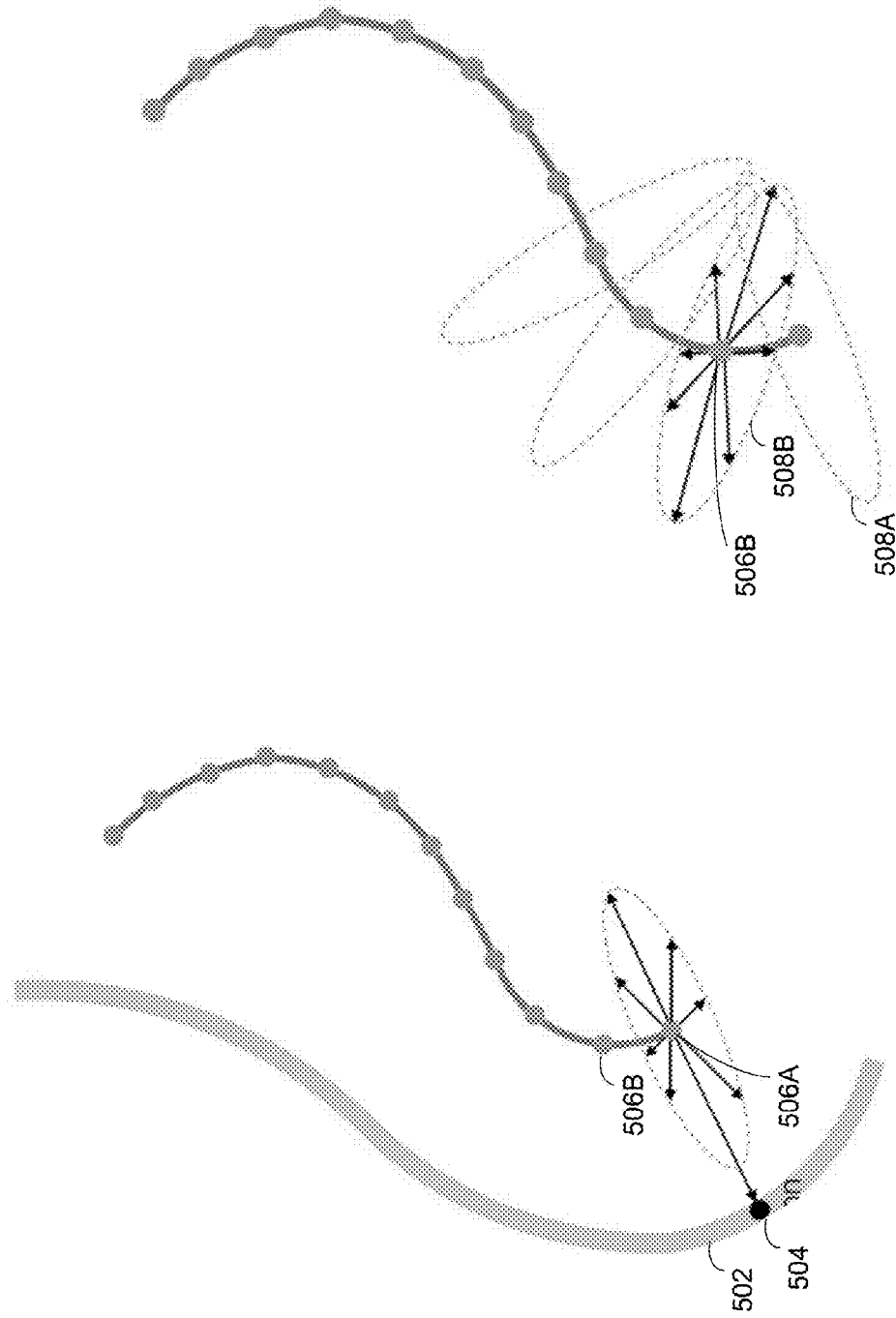

MATERIAL ANALYSIS OF ANATOMICAL ITEMS

RELATED APPLICATIONS

The present applications claims priority to U.S. Provisional Application 61/865,596, titled "Computer Modeling of Anatomical Items," and U.S. Provisional Application 61/865,407, titled "Multi-Touch Interface," both filed Aug. 13, 2013, the contents of which are incorporated by reference in their entirety.

TECHNICAL FIELD

This document relates to systems and techniques for viewing and manipulating models of body parts, such as human and other animal organs, so as to improve computer operation.

BACKGROUND

Medical imaging technologies allow physicians and researchers to visualize internal items inside the body of an animal subject. Such imaging technologies generally provide a two-dimensional representation of a slice through the body at a particular depth, or a projection of an entire body onto a two-dimensional plane (e.g., with x-rays). Typical modern, digital imaging techniques include magnetic resonance imaging (MRI) and computed tomography (CT) scans. In addition to producing images that can be colored for more ready interpretation, such scans can also produce data files that can be automatically analyzed and manipulated in various manners. For example, imaging data may be used to construct 3D jigs for use in dental and orthopedic procedures for a particular patient.

SUMMARY

This document describes systems and techniques by which users of a computer-based visualization system can manipulate and visualize anatomical items, such as organs (e.g., hearts and connected vasculature) from humans and other animals. Models of such anatomical items may be obtained from medical imaging of an actual subject, such as by obtaining digital data generated by magnetic resonance imaging (MRI) machines and computer tomography (CT) machines. Such data may be represented by a number of two-dimensional images at different layers of the item, as the imaging equipment scanned layer-by-layer through the item. The systems described here can identify common locations in images or models in the anatomical item from the two different medical imaging modalities, may generate a combination of the data, and may generate a 3D mesh of lines or points that substantially reflect the dimensions of the anatomical item. The systems may then generate a 3D model from the mesh.

In addition, imaging data may be captured at different points in the movement of the anatomical item, such as at a dozen or so points in time during a cycle of a heartbeat where the anatomical item is a heart. Those data from different times may be used to generate a three-dimensional model for each point in time, and those three-dimensional models may be joined together to create a four-dimensional model (i.e., three spatial dimensions plus time).

Such models may permit researchers or clinicians to analyze and manipulate an anatomical item in convenient, relatively inexpensive, and intuitive manners. As a simple example, a physician can order imaging for a particular patient, and may wear stereoscopic goggles to view the patient's heart from different angles. The physician may also introduce a cutting plane to the model so as to see the patient's heart from the inside —e.g., cutting horizontally across the atria, and then looking down into the heart from the top so as to see the motion and sealing of the heart valves. In some implementations, multiple models of the same anatomical item may be displayed to assist a user in better understanding the item. For example, imaging may be performed on a patient both before and after an operation or other medical procedure is performed on the patient, such as the implanting of a medical device like a stent or cardioverter. Three-dimensional or four-dimensional models of the anatomical item may then be displayed in 3D space adjacent to each other, and action by a user (e.g., a treating physician) with respect to the item may be reflected concurrently in both models. For example, if a user applies a cutting plane to see inside an atrium or inside certain vasculature in the post-op model, the pre-op model may have the plane applied in the same location (with each of the models having been positioned and oriented relative to a common base point). Similarly, a 4D model may be displayed concurrently with one or more 3D models that are based off the same imaging data (or where some of the models may use imaging data from a different time period for the same organ or other body part). The 3D models may be considered non-moving in that they are not animated, though all of the models may be panned, zoomed, rotated, or clipped in coordination with each other in response to user inputs. In this manner, for example, a physician could see the operation of a patient's heart valves in a 4D view and simultaneously view a 3D view that shows the heart with the valves closed —so that the physician can see the degree to which the valves close and can view a repeating cycling (similar to display of a GIF file that cycles) to try to determine mechanically why the valve is closing the way it is —with the 3D presentation at the particular point in time displayed adjacent the 4D representation that cycles over time.

Also, a physician or other user may select different points in space on a projected 3D model, and the system may compute the distance between those points, may snap to the edges of an opening near the points and compute the diameter, area, or radius of the opening, and/or may perform other similar measurements and may communicate the measurements to the user, such as by annotating the model with alpha-numeric characters that express the measurement. The measurement may also be expressed for a moving 4D model, such as via numbers that represent a maximum and minimum dimension across the range of motion at the points where the user made the selections.

Moreover, the interaction of the model with external items introduced to the model may be reviewed and studied. For example, a medical device may be introduced into the anatomical item, such as by inserting the device into an open passage in the item. As the device is moved, a physician or researcher can determine whether it interferes with tissue in the model, and to what extent it interferes. For example, a system may be programmed to identify an open path through vasculature leading into a patient's heart, in a model, and can insert a spline curve as a modeled representation along a centerline of the path. A geometric construct, such as a two-dimensional circle designed to be about the diameter of a planned implantable medical device, or a 3D model like that for a bendable stent (a flexible cylinder), may be run along the length of the curve. The system may track the location of the anatomical model and the model of the device, and determine whether they come into contact at any point.

If contact is made, the system may note it, and perform both mechanical and material analysis on any around the points of contact. For example, for mechanical analysis, a system may cause deformation of tissue to occur in the model using finite element analysis techniques, and may also change a display of the model so as to show the tissue moving in response to the stress, and perhaps changing the displayed color of the tissue, where the new colors represent the level of stress or strain on the tissue at particular points. The system may also deform the device in response to computed forces from the tissue, and may display the deformed device graphically in an animation and/or generate and save, and display alphanumeric representations of parameters for the forces on the device and the tissue and the deformation of each. The system may simultaneously compute fluid flow around the device using computational fluid dynamics and a 4D visual model may be supplemented with a visual representation of the flow (e.g., with projected flow lines indicating direction and speed of the flow). For material analysis, a system may identify electrical and chemical changes caused by the normal operation of anatomical item, and may adjust those changes so as to reflect the effect of the introduced medical device on the tissue. As one example, a medical device may change the propagation of electrical charge through a heart, and FEA or other techniques may be used to model the electric propagation. Similarly, when drugs are applied to the tissue, such as via a drug-eluting medical device, the effect of the drugs on the material properties of the tissue may also be calculated and used in a model to indicate the reaction of tissue to the introduced medical device. In processes like those discussed below, different simulations may be performed by selecting a medical device of varying materials, shapes, and/or dimensions (e.g., ever-increasing diameters and/or lengths) and determining mechanical (e.g., stress), electrical, or chemical values for each such simulation. A process may then indicate to an operator which of the simulations was performed with a highest or lowest value for a mechanical, electrical, and/or chemical parameter that is of interest to a user. Or a user may specify a threshold value for any such parameter, and the simulations may be performed to determine which provided inputs qualify. For example, a physician may set a maximum stress a medical device may place on tissue when the device is to be implanted, and simulations may be performed on multiple sizes of increasingly larger devices until the predetermined threshold is met. The physician may then employ a device of the last size that passed the simulation without exceeding the threshold.

The visualization and manipulation may be used by physicians, researchers, and others to better understand a procedure and to help others better understand it. For example, a physician may use such models to simulate a procedure for purposes of practice, to determine whether a particular medical device will seal well or mount well in a patient, and to identify a size of a device (e.g., a heart valve) that will best work with a patient. The physician may ask the particular patient to witness his interaction with the simulated heart or other anatomical item so as to educate the patient about the procedure —e.g., before the procedure has occurred. Similarly, medical device companies or expert physicians may use such simulations to train other physicians in new procedures, where, for example, an expert physician may initially perform the procedure one or more times on the model, and may then invite trainee physicians to attempt the procedure. Such simulations may also be useful outside the context of data for a particular patient, and a model may represent an average or idealized patient (or multiple idealized patients, such as five different patients have different representative dimensions and other parameters for their organ), such as during testing of a new medical device for government approval. For example, a typical heart may be modeled using an average of data from the imaging of a large number of hearts from many different patients, and such a typical heart may be used by a medical device company to demonstrate to a government licensing agency the feasibility of a new device or technique.

In certain implementations, such systems and technique may provide one or more advantages. For example, researchers and clinicians may better design medical devices to interoperate with a body, or may better select, size, or manipulate a particular medical device with respect to a particular patient's body. Such visualization may be used as a "dry run" for a complicated procedure and/or as an opportunity to explain the procedure to a patient and/or to train others in performing the procedure. Where FEA is used in such operations, the compliance of a patient's tissue may be modeled so that the tissue interacts with forces that a user (e.g., physician) places on it, such as by deforming in response to the introduction of a virtual medical device into a body (e.g., so that a researcher or physician can see how firmly the device seats when implanted or can see whether any gaps that could create leaks exist around the device).

In one implementation, a computer-implemented method for medical device modeling is disclosed that comprises accessing an electronic definition for a model of a three-dimensional item and an electronic definition of a three-dimensional spline relating to an internal anatomical volume; determining, with a computer-based finite element analysis system and using the electronic definitions, stresses created by the three-dimensional item along the three-dimensional spline, for different points along the three-dimensional spline; and displaying stress data generated by the finite element analysis system with a visualization system, the display of the stress data indicating levels of stress on portions of the three-dimensional item at particular locations along the three-dimensional spline. The three-dimensional item can comprise a model of a medical device, and the medical device can comprise a stent, with the model formed as a cylinder having a longitudinal axis that is aligned with an axis of the three-dimensional spline curve. The one or more stresses can be determined by a finite element solver that is external to the visualization system, and the finite element solver can be at a site that is separate from a site that houses the visualization system, with the finite element solver serving a plurality of different visualization systems at different sites, and communicating with the visualization systems over a network-based connection. Moreover, the method can include displaying multiple stress visualizations and corresponding anatomical models side-by-side with each other for visual comparison.

In some aspects, the stresses are automatically determined repeatedly for different splines having different shapes in one or more anatomical models. Also, the method can additionally comprise determining, using computational fluid dynamics techniques, information describing flow characteristics for fluid flowing through the internal anatomical volume. The information describing flow characteristics can be generated by determining fluid flow around the three-dimensional item. In addition, the method can include identifying electrical characteristics for tissue surrounding the internal anatomical volume, and determining the stresses as a function of the electrical characteristics. The electrical characteristics can comprise electrical charge propagating over time through heart tissue as part of a cardiac cycle.

In yet other aspects, the method includes, for each particular point of a plurality of points along a path through the internal anatomical volume, automatically performing operations that comprise: generating a plurality of rays around the particular point in a common plane; and determining lengths of each of the plurality of rays from the particular point to a boundary of the internal anatomical volume. The method can also comprise moving the three-dimensional item along the three-dimensional spline, and visually representing the three-dimensional item as it is moved along the three-dimensional spline. In addition, the internal anatomical volume can be defined by a model of an anatomical item generated by operations comprising: obtaining data that represents imaged two-dimensional slices of the anatomical item captured by one or more medical imaging systems; generating an intermediate three-dimensional representation from points identified in the two-dimensional slices; and generating the three-dimensional model from the intermediate three-dimensional representation.

The details of one or more embodiments are set forth in the accompanying drawings and the description below. Other features and advantages will be apparent from the description and drawings, and from the claims.

DESCRIPTION OF DRAWINGS

FIGS. 5A and 5B show schematically a computation of distance from edges of an anatomical item to a 3D spline curve.

Like reference symbols in the various drawings indicate like elements.

DETAILED DESCRIPTION

Figure 1:
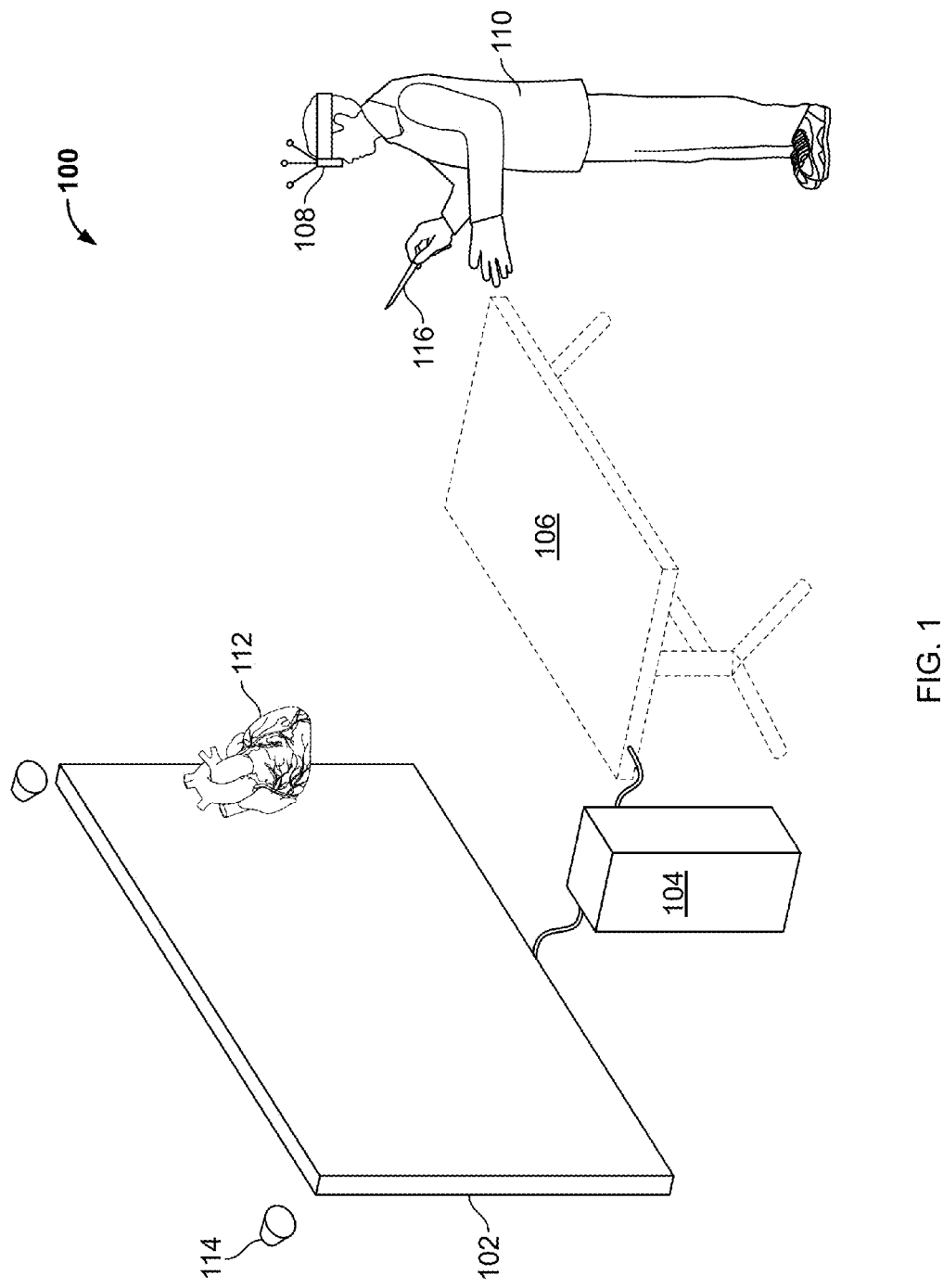
FIG. 1 is a conceptual diagram showing a user interacting with a visualization system.

This document describes systems and techniques for visualizing anatomical features of animals, such as human hearts and vasculature, and other organs on which medical procedures are frequently performed. The visualization may include generating 3D projections for viewing by users wearing stereoscopic goggles or other mechanisms for realistic viewing of 3D or animated renderings, and 4D animations that show cycling of an organ, such as an entire heartbeat for a heart, where each frame of the 4D animation may be generated from data capture at corresponding relevant times during which the relevant anatomical feature was imaged.

Users may interact with the models of the anatomical features in various manners. For example, a user can zoom in and out and rotate a model so that they appear to view it from different angles and different distances. They may apply cutting planes to the model, including multiple simultaneous non-parallel planes, so that they can see internal cross sections of a model—e.g., to see the inside of vasculature or the inner operation of a heart or lung. They may "draw" on the model such as by having a system add geometric constructs around and through the model. For example, a system may build a spline curve that passes through the vasculature in a model, and into a heart. Such additional geometric constructs and other meta data for a model may be stored by a system in relation to the model, so that when the model is closed and then subsequently opened on a computer system, the meta data may be immediately displayed (e.g., as graphical and/or alphanumeric annotations on the model) or at least immediately available to a user without having to redefine the data (e.g., the route of a spline curve may be saved, as may parameters for a medical device to be moved along the spline curve, so that those features may be preexisting when a user opens the model for subsequent sessions).

In other examples, a system may be able to create and align best-fit registration to a defined coordinate system with three or more markers in each data set, including the ability to synchronize multiple data sets. For example, a user may select three reference points on a heart to associate the coordinate system, may do the same with another heart, and the system may use such selections to display and move the two hearts together in coordination in a common coordinate system. In other words, the two hearts may be locked together for manipulation so that panning or rotating of one model causes an equal panning or rotating of the other model. In certain instances, one of the models may be 4D and the other 3D, such as a fixed frame from the 4D animation.

In another example, multiple animated models may be displayed and interacted with by a user simultaneously. For example, a model of a healthy organ may be shown in animation adjacent to a model for a particular patient's organ (e.g., heart or lung). The two models may be locked with each other, both in position as discussed above (e.g., if one is rotated by a user, the other automatically rotates in the same manner), and also in the location and timing of their cycling—e.g., so that models of two hearts begin systole and/or diastole simultaneously (where the animation repeatedly cycles through one heartbeat or a set number of heartbeats, and then starts again). A physician could use such a display of dynamic action of both models to better see abnormalities in the patient's organ.

FIG. 1 is a conceptual diagram showing a user interacting with a visualization system 100. In general, the system 100 provides an environment by which a user 110 may view a 3D representation 112 of a model of an anatomical item, such as a human organ in the form of the human heart. The 3D representation is generated by projecting a computer-generated image on a screen 102 under control of computer system 104. The user 110 may interact with the computer system 104 through a touch tablet 106, which may be horizontally-mounted in front of the screen 102 and may include an additional display of the item, along with a number of menu selections made available to the user 110. For example, one or more lines may be presented on the touch tablet 106, and a user may slide the lines across the touch tablet 106 by touching the end of a particular line and dragging in contact with the screen of the touch tablet 106. Such dragging may cause a line to intersect a 3D or 3D representation of the model, and may cause the computer system 104 to apply a cutting plane to the model so that the user 110 can see an interior portion of the model.

Sensors 114, which may be implemented as cameras aimed at user 110 and stereoscopic glasses 108 worn by the user 110, may be employed to track the position of the user's head so as to make the 3D presentation of the model more realistic for the user. For example, the sensors 114 may recognize when the user 110 tilts his or her head, or moves laterally in front of the screen 102. Such sensed motion may result in the computer 104 adjusting a display of the model 112, such as rotating the display to the right when the user 110 is determined to have moved to the left, so that the user receives the visual impression that he has moved slightly around the model to the left, and is better able to see down into part of the model, for example.

Various mechanisms other than touch tablet 106 may also be used to obtain input from the user 110. For example, a stylus 116 may be grasped by the user 110 and its position may be sensed by sensors 114 or other sensing mechanisms. The stylus 116 for example, may have its location identified and the system 100 may project a virtual line that looks to the user 110 as if the line is extending out from the end of the stylus 116. The user 110 may move that virtual line into contact with the model and may make a selection, such as by clicking a button on the side of the stylus 116, so as to grab the model 112. Subsequent motion by the user of the stylus 116 while holding down the button may cause the model to be moved in space in front of the user 110. For example, if the user 110 pulls the stylus 116 toward his face while holding down the button, the model may be caused to get larger so as to seem like it is being brought closer to the user's 110 face. As an alternative, if the user rotates his wrist while holding a button on the stylus 116, the model may be rotated in a similar direction, so that the user may manipulate it to see other areas of the model 112 that were not previously visible to the user. Other intuitive gestures may also be employed by the user 110 to manipulate the model. For example, the user may use the stylus 116 to draw lines, curves, or other geometric constructs in the area of the model 112, such as by drawing a line through open areas of a heart to define passages through the heart. Such lines may be presented in a color that contrasts with that in which the model 112 is being presented, so that the user 110 can readily see the lines and other geometric constructs that the user 110 has added to the overall model.

Yet other mechanisms may also be used for interacting with the system 100. For example, the user 110 may wear a glove that serves a similar role to that of the stylus 116. For example, the user may reach out to grab the model 112 with a glove, and the display of the model 112 may make it appear to the user 110 as is if the user 110 is actually gripping the model, so that the user may, for example, rotate the model left or right or push the model away from him or toward him. Such input mechanisms may also be provided with mechanisms for applying haptic feedback to a user. For example, a stylist 116 or glove may have a haptic clicking mechanism that is energized when a user is determined to have gripped a model or to have moved from one area on the model to another, so as to confirm to the user 110 that the system has registered such actions by the user. A particular implementation may also be seen discussed in more detail below in FIGS. 5A and 5B.

Figure 2:
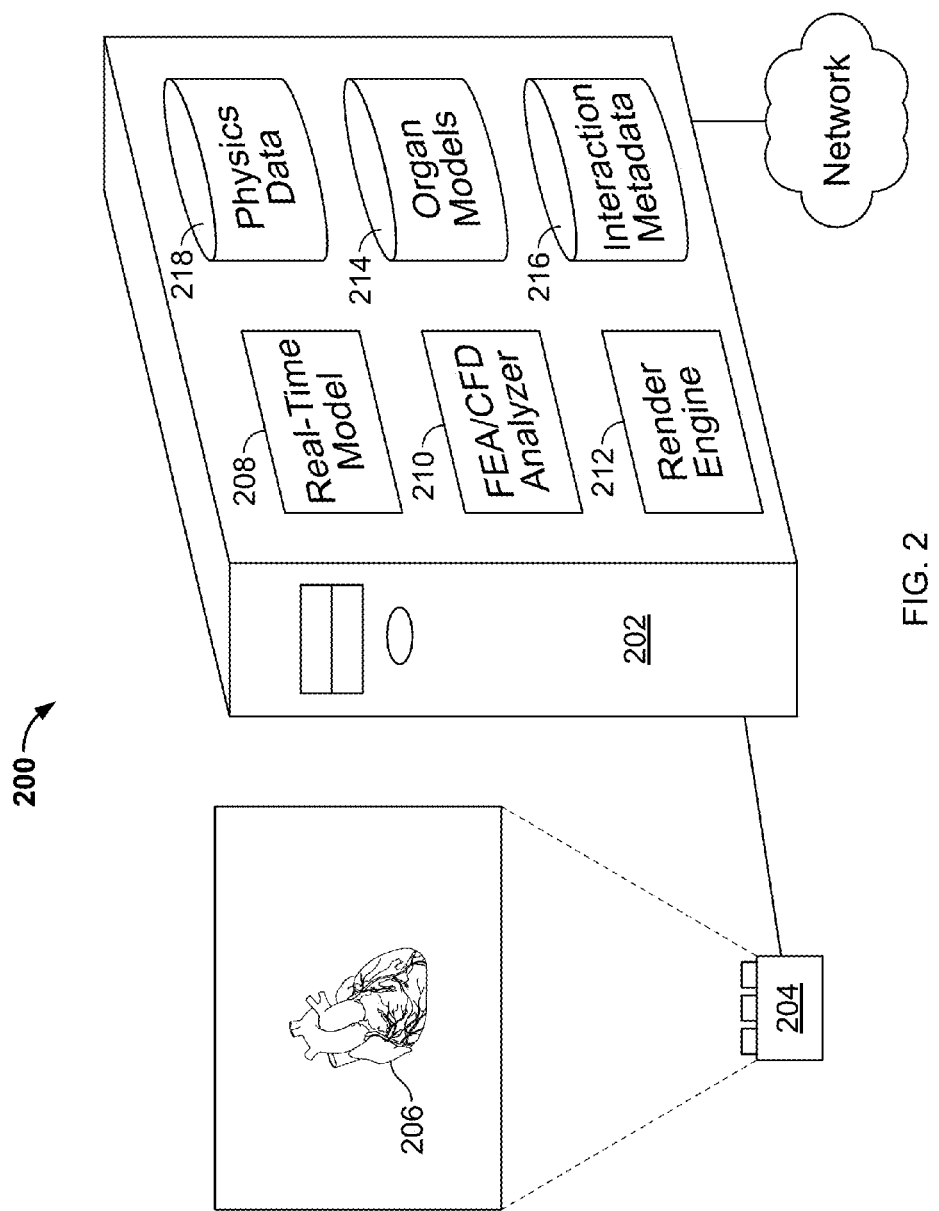
FIG. 2 is a block diagram of an illustrative visualization system.

FIG. 2 is a block diagram of an illustrative visualization system 200. The system 200 may implement components of system 100 in FIG. 1, but particular structural components of the computer system used to generate multi-dimensional renderings are shown in more detail here for additional clarity in explanation.

The system 200, in this example, comprises a computer system 202 that drives an imaging system 204 in the form of a standard projection television system having 3D display capabilities. The result of such driving is the display of a 3D model 206 in an area where a user, such as a clinician or medical researcher or patient, may view the model and may interact with the model in a variety of manners such as those discussed above and below. To permit such display and interaction, the computer system 202 includes a number of structures that interact with each other.

A real-time model 208 is a module in the system 200 that accesses data concerning one or more models of anatomical items, such as a heart or other organ of the human or other animal, and performs computations on the model to generate data that is capable of producing an accurate visual rendering of the model. For example, the real-time model 208 may include mechanisms for accepting a definition for a model and for performing various operations on the model, such as distorting the model, clipping the model, blending the model with other models, and other similar operations.

Information from the real-time model 208 may be provided to a render engine 212, which may be implemented as software, hardware, or a combination of the two. For example, the render engine 212 may include one or more graphics processing units and associated circuitry, such as that mounted on a commercially-available graphics processing card provided in a personal computer or mini-computer. The render engine 212 may operate according to standard protocols and definitions for modeling 2D, 3D, and animate materials for a 4D display (a 4D representation). For example, the render engine 212 may apply shading and other known techniques for generating a photorealistic display of the model 206.

A finite element analysis, computational fluid dynamics analyzer 210 may be referenced by the real-time model 208 where an anatomical item needs to be provided with compliance, such that stresses applied by a user on the item result in deformation of the item in computationally predictable manners, or result in deformation of tissue for the anatomical item. For example, a user of the system 200 may invoke a 3D model of a medical device, such as a stent or similar device, and may move or have the device moved through the model 206, or placed in a particular location in the model 206. Such placement or movement may cause the device to contact tissue in the model 206, and the analyzer 210 may be used to compute the forces applied by the device on the tissue, and the reaction of the tissue to such forces. For example, a model of a mesh stent may be expanded against the walls of a model of a patient vasculature, and the color of the vasculature in a display made by the system 200 may change to highlight where the stresses or strains are the highest or lowest on the wall, such as by generating a heat map whose different colors represent particular degree of stress or strain.

The finite element analysis, computational fluid dynamics analyzer 210 may perform both mechanical, electrical, and chemical analysis, and may interrelate those analyses with respect to the manner that they may affect each other. For example, tissue compliance may be used in determining mechanical stresses and strains from introduction of a medical device. Electrical activity of the tissue may be modeled for its own purposes, and also to determine how inherent motion of the tissue (e.g., heart tissue) affects how it will deform or otherwise react to introduction of a medical device. Similarly, the introduction of chemicals, such as local or systemic administration of drugs, may affect the action of the tissue, such as by changing its mechanical compliance or changing the way that electrical propagation occurs through it. Such introduction of chemicals may thus also be included in a model that determines how the tissue reacts.

The system 200 may also be programmed to recursively perform multiple simulations that involve automatically passing simulated medical devices through one or more anatomical items, using the computational and modeling techniques described here. Such simulations may employ the finite element analysis, computational fluid dynamics analyzer 210 to identify results of such simulated actions, including results represented by mechanical, electrical, and chemical activity. For example, increasingly larger sizes of stents may be moved through and placed in one or more anatomical items, and stresses and other factors may be computed as the motion of the device occurs. Thresholds for mechanical, electrical, or chemical parameters may be set by a user of the system 200 or by another (e.g., a developer of analysis software) to define acceptable versus unacceptable performance, such as a threshold that indicates when mechanical stresses on tissue are too high, or an electrical propagation threshold—either of which are exceeded, for example, once the simulated device becomes too large. The system 200 may then identify the proper device as the last in a progression of every-increasing-in-size simulated devices that did not cross a threshold into an area of unacceptability.

The various structures already discussed may depend on one or more types of data in performing the actions described above and below. For example, organ models 214 may represent data for one or more organs of a subject, where the subject may be a patient who has had medical imaging performed one or more times on their body. The organ models 214 may include data that represents spatial relationships in a portion of the anatomical item, in addition to information about tissue compliance and other similar information for the patient or other subject.

Interaction metadata 216 may represent data that is generated in response to the interaction with a patient model by a physician or other user. For example, a user may make various measurements of a model and the locations and values of those measurements may be stored so that they may be easily retrieved later by the user. Similarly, a user may form various geometric constructs, such as lines, arcs and other constructs in relation to the model 206 in space. For example, a user may draw a line or spline through passages in an organ or other anatomical item. The system may also create such constructs automatically, such as by a user pointing to a passage through which they would like a spline to be drawn, and then the system identifying the boundaries of the passage and constructing a spline roughly through the center of the passage—e.g., computing the center of the passage at a plurality of different locations, and then fitting a spline curve to the plurality of centerpoints that are so identified. Similarly, a user may insert particular CAD blocks (CAD representations that include multiple geometric constructs that are tied together and that represent a complex, real-world object) in an organ or other structure, such as blocks that represent medical devices to be implemented in an anatomical item. Definitions for those blocks, and locations and orientations of the blocks relative to the model 206 may likewise be saved in the interaction metadata 216, so that a user may readily show the blocks in position in the model 206 during a later session with the system 200.

Physics data 218 may include data that is necessary for representing physical interaction by a user with the model 206. For example, tissue compliance information may be stored in the physics data 218 for typical types of tissue, such as vasculature and cardiac tissue in various states of deterioration or patient age. Thus, where finite element analysis is employed for system 200, particular tissue values from the physics data 218 may be used, rather than values that may be specific to the particular patient Similarly, the physics data 218 may include data for modeling the effect of electrical activity and of chemical activity.

The computer system 202 may also obtain data from external sources via network 220, which may include a local area network, and portions of the Internet. For example, the computer system may obtain imaging data for a particular patient by accessing a cloud-based storage system where the company that did the imaging stores its data for access by users who can provide proper credentials for accessing the data.

In this manner, then, the system 200 may provide for various mechanisms for displaying models alone or together with other models, and for various users to interact with the models. The system 200 may allow users to better visualize, and thus be better able to understand, relatively complex physiological interactions, and to appreciate actions that occur inside a body and outside of normal human sight.

FIGS. 3A to 3J are flow charts of example processes for interacting with an anatomical feature displayed on a visualization system. In general, the processes may be performed using a system like system 100 in FIG. 1 and/or system 200 in FIG. 2, in addition to the systems and user interfaces represented in FIGS. 4A to 4L. These are example processes that involve user interaction with a multi-dimensional computer-based visualization system. In general, the processes will be described as being carried out on a human heart of a particular person being treated or analyzed by a physician, but it should be understood that other physiological items may be modeled and presented, including from non-human animals (e.g., for porcine hearts that are part of engineering development studies for a medical device), and for analysis by a variety of users and for a variety of purposes (e.g., physician practice, medical device sizing for a particular patient, education, regulatory approval, etc.).

Figure 3A:
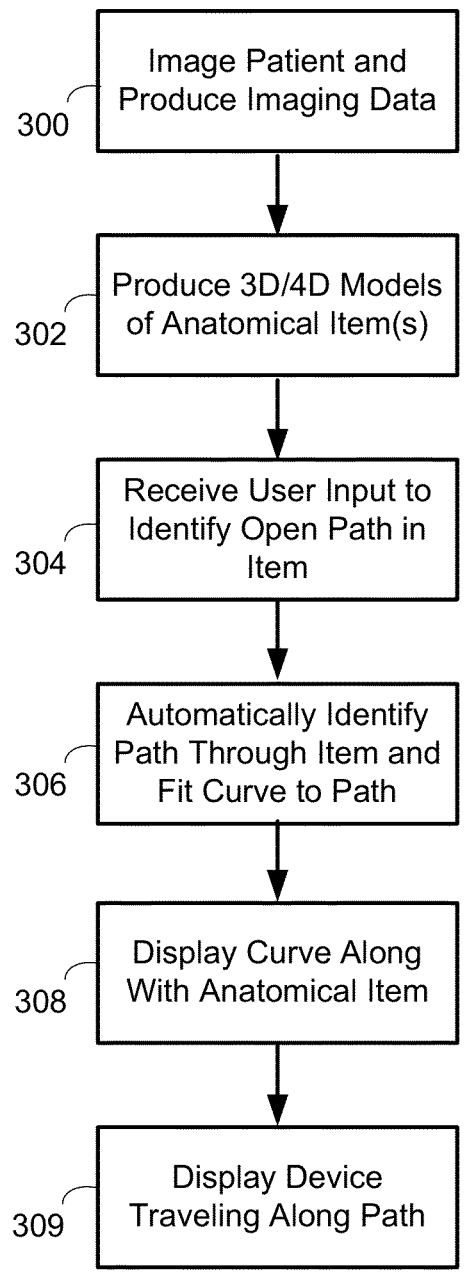
FIGS. 3A to 3J are flow charts of example processes for interacting with an anatomical feature displayed on a visualization system.

FIG. 3A is a flow chart of a process for identifying and using a path through an anatomical item. In general, the process involves a system displaying a view of a model, and the system in cooperation with a user defining a path through a part of the model for various purposes.

The process begins at box 300, where a patient is imaged, and imaging data is produced for that patient. Such imaging may occur, for example, using multiple different imaging modalities, including MRI and CT scan imaging. The data produced from such imaging may be in a digital form and may represent slices at different elevations through a part of the patient. Lines in such images may be used to identify the boundaries of anatomical items and other items captured in the images.

The generation of a 3D model may occur by a variety of mechanisms, including iso-surface extraction. The iso-surface extraction may be interactive by a user of a visualization system. For example, such extraction may include multiple steps that involve generating and refining a 3D surface using a touch-based 2D interface coupled with a 3D display. In a first step, a computer system may generate a 3D surface from a stack of imaged slices, where each slice comprising a medical image acquired from an imaging modality (e.g., CT, MRI, etc.). In a next step, the system may render the 3D surface on a 3D display using an iso-surface extraction run on a computer graphics processing unit (GPU) to create an interface to allow a user to virtually touch a visualization of a slice. In such an example, the iso-surface extraction can be based on iso-values derived from the stack of slices. In response to receiving user input interacting with a slice from a user operating the interface, the system may calculate a refined iso-value used for the iso-surface computation that is based on the input. The system may then refine the 3D surface based on the refined iso-value for the iso-surface. Such a process may loop continuously as a user interacts with the displayed model via the interface at box 302, 3D and 4D models of the anatomical items captured in the imaging are produced. Such production of models may occur, for example, by identifying lines in the images of particular slices and placing dots or vertices for a mesh at spaced locations along such lines where the image changes intensity or color. The vertices may then be connected to form a mesh, and the mesh may be changed into a solid model that represents the anatomical item. Certain areas of the model may be identified as being filled, in other words, being locations where there is tissue from the anatomical item. Other locations may be identified as voids, such as chambers in a heart or through vasculature, or similar open spaces in a patient.

At box 304, user input is received to identify an open path in the anatomical item. Such input may include the user drawing a path through a cross-section of the anatomical item that is displayed on a computer system. Alternatively, the input may occur by the user instructing the computer system to find a best path through the item automatically, and the computer system identifying the voids in the model and fitting a curve through such voids from a first defined location to a second defined location, such as through an aorta and into one or more chambers of the heart. In some implementations, a number of common routes that physicians use often may be presented to a user in a list, the user may select one such path (e.g., a path for delivery of a stent or a heart occlusion device), and the system may automatically generate and display a spline along that path for the particular model—e.g., by identifying open space in the particular model whose size and shape roughly fits a template for such portion of the anatomical item (e.g., particular diameter and particular curvature, such as for an aorta and heart chamber).

At box 306, the system automatically identifies the path through the item and fits a curve to that path. For example, an initial path may be identified, and points along the path at a center point of the void may be identified at a plurality of spaced-apart positions along the path. A geometric CAD tool may then be used to fit a curve in a best fit manner to those points. The system may also confirm, after the curve has been formed, that the curve does not pass through any tissue in the anatomical item. Other mechanisms may similarly be used to identify a curve through the path that stay adequately within the voids in the anatomical item. Particular details for making such determinations are discussed in more detail below with respect to FIGS. 5A and 5B, and may be incorporated into the process described here.

At box 308, the curve is displayed along with the anatomical item. For example, the anatomical item may be displayed in various shades of red to represent tissue in a realistic manner, and the curve may be represented as a blue or green line that visually contrasts with the color of the tissue. The curve may be defined in the same 3D space as is the model, so that a user who manipulates the model, such as to rotate themselves around the model, may also rotate themselves around the curve in a similar manner (i.e., the curve moves with the model and stays in the same 3D position with respect to the model).

At box 309, a device is displayed traveling along the path. The device may be as simple as a circle having a defined diameter (provided from the user) being slid along the curve. A more complex device, such as a block that represents a 3D model of a stent or other medical device may be moved along the curve and may bend or otherwise deform as it is moved so as to approximate the shape of a real stent being introduced into a patient. Such display of the device may be used, for example, by a physician who may select different diameters for a stent or similar implantable device, and may simulate the insertion of the different diameters into the patient by way of the model (e.g., to determine which size of a medical device should be selected for a particular procedure). A physician may thus more readily see which size of device may work the best for a patient, and may avoid trial-and-error that may have otherwise been required in performing the actual procedure on the patient.

The device may also be defined to have certain mechanical, electrical, and chemical characteristics. For example, the device may have certain stress/strain characteristics, such that bending it along a spline requires extra force. Similarly, the device may be coated with a drug-eluting material, and the behavior of such material may be modeled, so that a simulation of moving the device through an anatomical item may also indicate a level of drug that is passed from the device to the item.

In addition, the thing that is moved through and along the spline may simply be a virtual camera that a user of a visualization system may manipulate using the hardware and software described above and below. The camera may be anchored to the spline so as to simplify user input, such as by employing motion of one hand of a user to pan the camera forward and backward along the spline, and employing motion of the user's other hand to accomplish rotation of the field of view of the camera.

Where the model of the anatomical item is moving in time (a four-dimensional model), such as a beating heart, the device and spline may be moved to maintain their positions relative to the anatomical item in time (e.g., so that the spline and device stay positioned in an open area, such as a heart chamber or vasculature). Also, such motions may change mechanical, electrical, and chemical parameters that are computed for the model, as are described above and below.

Figure 3B:
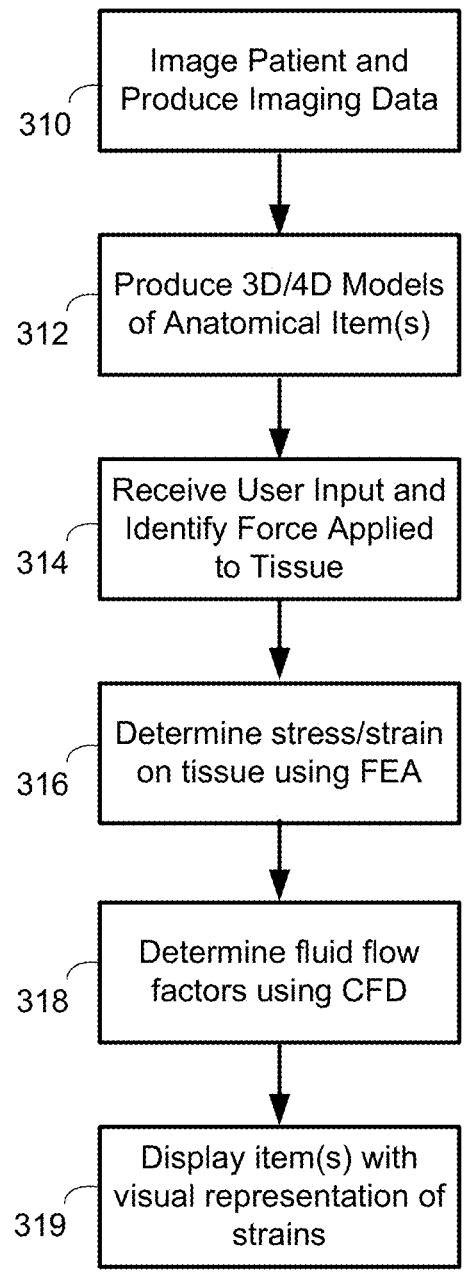

FIG. 3B is a flow chart of a process for identifying forces and actions around a model of an anatomical item. In general, the process involves identifying a model of an anatomical item, identifying forces applied against the model, such as by identifying a medical device that is introduced into the anatomical item and interacts with surfaces in the anatomical item, and modeling the reaction of tissue in the anatomical item using finite element analysis techniques. Such interaction may then be represented to a user of a computer visualization system, such as by showing colored heat maps, where different colors represent relatively greater or lesser degrees of stress or strain on the anatomical item.

The process begins at box 310, where a patient is imaged in a healthcare facility and imaging data for the patient is produced. Such production of imaging data may occur in a manner like that discussed for FIG. 3A. At box 312, 3D and 4D models of the imaged anatomical items for the patient are produced. For example, a 3D model may be prepared as described above, while a 4D model may be prepared in a similar manner, but may exist as multiple different models presented in sequence over time, where each of the multiple different models represents a separate imaging of the patient over that time period, where the time period is relatively short, and obtaining a single imaging session. For example, the time period may be the period of a single heartbeat, such as on the order of one second.

At box 314, a user input is received, and force applied to the tissue of the anatomical items is identified. Standard finite element analysis techniques may be used, such as by identifying interference between a moving model of a medical device in a passage of an anatomical item, and the distance that the moving device displaces tissue in the anatomical item. The device itself may also be compliant such that it is distorted in response to pressure from the tissue as it is moved through the anatomical item.

At box 316, the stress and strain on the tissue and on the device may be computed using finite element analysis. Such computations may be performed in conventional manners using data about the tissue and medical device compliance, as applied to information from the model showing degree of movement in the tissue and the device.

In addition to basic finite element analysis on the tissue as a static item whose properties do not change, other analysis may also be incorporated, including electrical and chemical analysis. For example, the propagation of electrical energy through a heart as tissue may be modeled (e.g., using finite element analysis), and may be used to affect the compliance of the tissue and the forces exerted on and by the tissue. For example, as the heart is a muscle, it may generate its own forces against a medical device, and such forces change in a cycle every second. From such activity, a dynamic model may be generated for a system by which electrical propagation is used to determine muscle contraction and to then model the forces from and on the heart and from and on the medical device.

At box 318, fluid flow factors in the anatomical item and around the medical device may be computed using computational fluid dynamics. For example, the amount and timing (because the heart is constantly changing) of blood flow pressure in human vasculature may be modeled, and may be adjusted to match the expected flow for the particular patient (e.g., by determining via blood pressure measurement and other measurements, the flow at a particular location and the strength of the patient's cardiovascular system). The open cross-sectional area at particular points along the modeled path may then be determined, such as around the perimeter of a medical device inserted into the modeled vasculature. From such data, a flow computation may be performed. The computation may then be updated for multiple time periods during a cycling, such as during a heartbeat cycle.

At box 319, the anatomical item or items are displayed with visual representations of the computed values. For example, areas of greater stress or strain on an anatomical item may be shown in colors that come closer to a red end of a spectrum, whereas lower levels of stress or strain may be shown by colors that come closer to a blue end of the color spectrum. Similarly, in a void of an anatomical item where fluid is flowing, such as in a chamber of the heart, flow lines may be displayed either in a 3D representation or an animated 4D representation, showing the direction and magnitude of flow for particular locations, much like meteorologists display flow lines on a map to show direction and magnitude of wind at particular geographic locations.

Figure 3C:
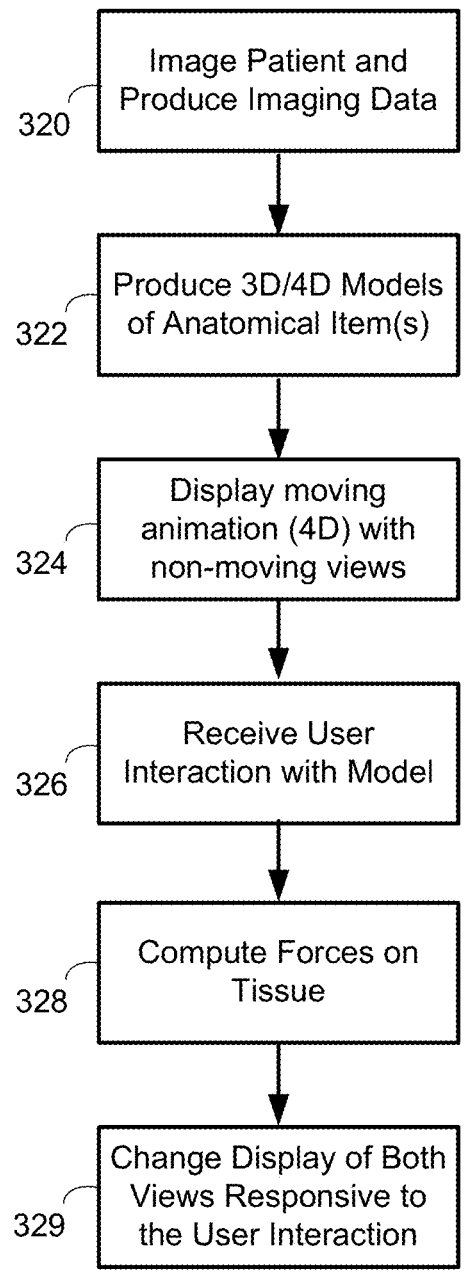

FIG. 3C is a flow chart of a process for coordinating displays of multiple models. In general, the process involves displaying two representations of a common anatomical item simultaneously so as to improve the ability of a user to visualize what is occurring with the model in interaction with the user.

At box 320, a patient is imaged and imaging data is produced, such as in the multi-modality imaging and modeling described above. At box 322, 3D and 4D models are produced such as in manners discussed above, from the data that is created from the imaging process.

At box 324, a computer-based visualization system displays a moving animation of the anatomical item or items while concurrently displaying one or more nonmoving views of the item or items. The nonmoving views may be 3D models that are not animated, and are viewed from particular angles and perhaps with particular cutting planes applied, or slices from the imaging data presented in two dimensions. This combination of display of a 4D representation with a concurrent display of a 3D representation may allow a user to achieve both a dynamic and static view essentially simultaneously. For example, the user may review the animated representation of the model to obtain an understanding of how the anatomical item works in general, and to find a hint of issues with the anatomical item, and then may quickly switch his focus to one of the nonmoving versions or views of the model so as to focus in on a part of the model and more readily sense it in the representation that is not moving. The user may also step through frames for the 3D model (while the 4D model continues to cycle) to get to a point in time that is of most interest, such as when an aortic valve is fully closed. The user may likewise pause the 4D representation, and may have the system copy the 3D representation that is part of that paused presentation, so that the copied representation replaces a 3D representation that had previously been displayed next to the animated 4D representation.

At box 326, a system receives user interaction with the model, such as a user introducing a virtual medical device into a model of an anatomical item. At box 328, the system computes forces on tissue of the anatomical item, such as in manners described above and below. At box 329, a display is changed with respect to both the 4D representation and the 3D representation for the anatomical item. For example, if a device like a tissue valve or mechanical valve is inserted into a heart, the animation may change so as to show the opening and closing of the valve and the movement of the heart tissue around the perimeter of the valve. In addition, a nonmoving representation may change to show the valve seated in position, and may also show coloring on the tissue to represent strains imposed on the tissue at particular locations by the presence of the valve in its implanted state.

Figure 3D:
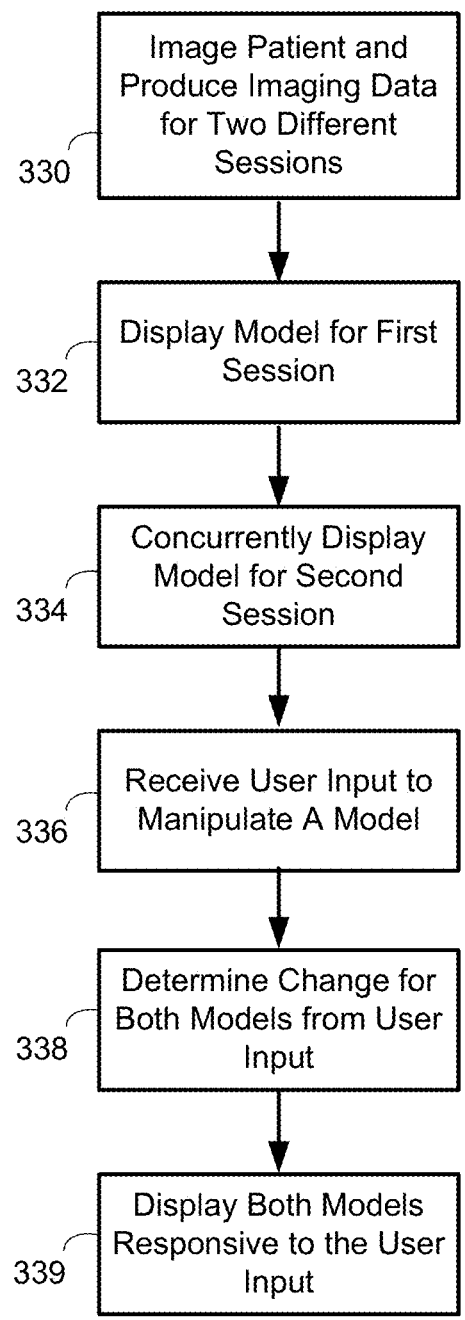

FIG. 3D is a flow chart of a process for coordinating displays of multiple models. In general, the process involves concurrently displaying models of an anatomical item, where the anatomical item was imaged in two different sessions for a patient. In one typical example, one of the sessions may have been pre-operation, and another may have been post operation, so that the comparison allows a physician to see how the anatomical item has reacted to the procedure, and to determine follow-up that may be required with the patient.

At box 330, the patient is imaged in two different sessions at different points in time (e.g., more than a day apart) and imaging data is produced from the imaging process such as in manners discussed above.

At box 332, a model for the first imaging session is displayed on a computer-based visualization system, and at box 334, a model is displayed concurrently for imaging from the second session. For example, a pre-operative model may be displayed on the left of a screen, and a post-operative model may be displayed on the right.

At box 336, user input to manipulate one or both of the models is received. For example a user wearing a haptic glove may reach out to grab one of the models so as to rotate it. In response to such user input, at box 338, the system determines a change for both models from the single user input. For example, if the user grabbed a right-hand representation of a human heart and rotated it 90 degrees clockwise, the system may determine that both displayed models of the heart should be rotated 90° clockwise.

At box 339, both models are displayed responsive to the user input as just discussed. Using this process then, a physician or other user may readily display a patient organ or other item as it was in existence at two different points in time, and may readily interact with those displayed models of the item so as to determine how the item has changed between the two points in time—e.g., by worsening or improving in physiology or by having a medical device implanted. As another example, the item may include a part of the patient body with a tumor in it and a physician may manipulate the area around the tumor, such as by panning around the tumor visually, to better appreciate how the tumor has grown or shrunk, and to better determine what sort of action should be taken with respect to the tumor.

Figure 3E:
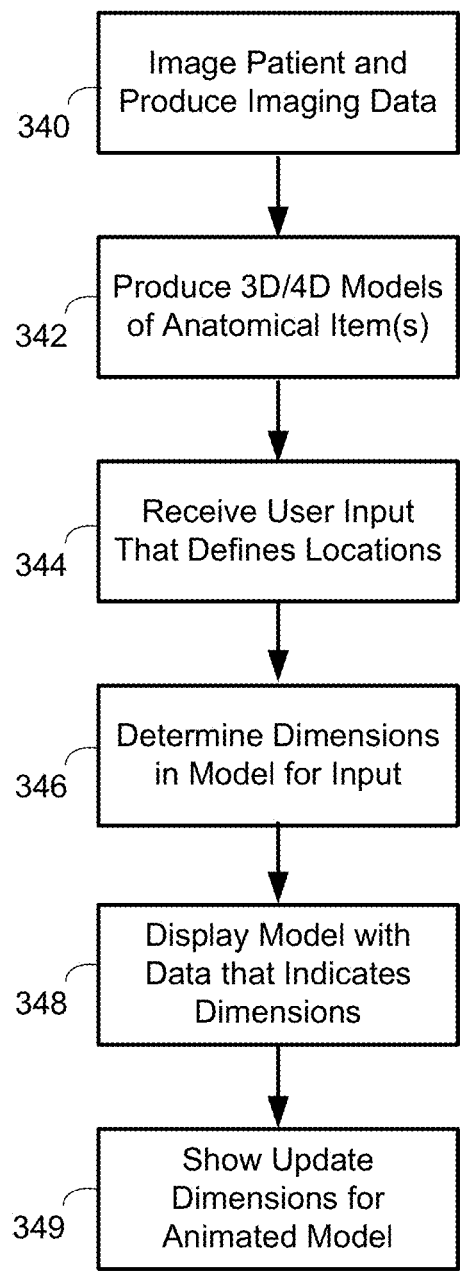

FIG. 3E is a flow chart of a process for providing measurements of a model. In general, the process involves a user making selections in a 3D display or 4D display of a model of an anatomical item, and a system making various measurements based on those selections.

At box 340, a patient undergoes medical imaging and imaging data is produced from such a process, such as in the manners discussed above. At box 342, 3D and 4D models of anatomical items captured in the imaging are produced. At box 344, user input is received at a computer-based visualization system, where the user input defines locations proximate to the displayed models. For example, a user may employ a stylus to point a virtual line at one wall of a vessel and then an opposite wall of the vessel. The system may be programmed to understand that such opposed locations indicate a desire by the user to determine a diameter of the passage at the selected locations or near the selected locations. The model may then be interrogated to identify the distance in two or three dimensions between the selected points, after identifying points that are adjacent to those selected by the user by that define a line perpendicular to a line through the passage (so that the diameter measurement uses too directly opposed points even if the user did not point at directly opposed positions). Such distances may correspond to the actual distance within the anatomical item in the real-world, such as being on the order of less than an inch even when the model appears to the viewer to be several feet across, because the viewer has zoomed in on the model as part of the visualization session. Other similar 2D or 3D or 4D measurements may also be made, including computing the volume of a chamber of a heart, computing the cross-sectional area of vasculature and other measurements that may be desired by a physician or other user.

At box 348, the model is displayed with data that indicate the dimensions that have been determined. Such display may occur in multiple different manners. For example, an arrow may be drawn across the diameter of the passage that the user has selected, and data may be overlaid on the arrow representing, for example the diameter of the passage in millimeters, centimeters, or inches. Separately, an annotation box may be displayed elsewhere in a visualization representation, away from the display of the model itself. For example, a small spreadsheet may be generated and displayed that represents the measurements computed by the system in response to the user input—e.g., diameter measurements every x millimeters along a user-defined path.

At box 349, additional representations may be made within a visualization system where a model is animated. For example, where a user attempts to determine a diameter of the passage, the diameter may be constantly changing in an animated model. As such, the system may be programmed to identify the diameter at every frame in the animation and to provide feedback to a user consistent with such determination. For example, a selection may be made in a 4D model, and the system may generate a 3D model adjacent to the 4D model, where the 3D model is annotated with dimensions. Such annotations may include two numbers for each such dimension, where one number is a maximum and another number is a minimum during a cycle represented by the animation, such as a single cycle of a beating heart.

Figure 3F:
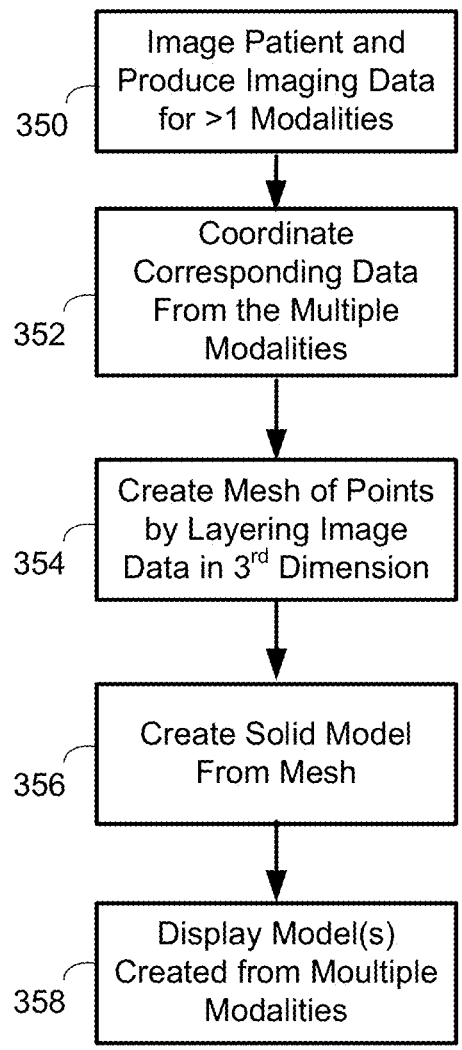

FIG. 3F is a flow chart of a process for generating a solid model of an anatomical item. In general, the process involves capturing data from multiple imaging modalities, correlating and analyzing the data, and then building a multiple-dimensional model out of such coordinated data from multiple imaging modalities.

The process begins at box 350, where a patient is imaged using multiple modalities, where a modality is a particular style for imaging. Typical such modalities include magnetic resonance imaging (MRI) and computer tomography (CT) imaging. Multiple modalities may be used because certain modalities may have particular strengths relative to other imaging modalities.

At box 352, data from the multiple modalities is coordinated. For example, images from the data may be analyzed to identify locations in an anatomical item that are the same as between two different imaging modalities. Such analysis may include identifying an outline of an anatomical item and matching it to an image from another modality having a similar outline. Such matching may be simplified if one knows from the imaging data the direction at which the particular anatomical item was imaged and matching it as between the two modalities, i.e., the item was imaged from the same direction for both modalities.

At box 354, a mesh of points is created by layering image data in a third dimension. For example, slices may be analyzed in the order that they were stacked for the actual anatomical item, and nodes for a mesh may be identified along boundaries in each of the slices. The nodes may then be stacked in a vertical dimension and may together form a mesh that substantially defines the anatomical item.

At box 356, a solid model is created from the mesh, and at box 358, a model is displayed that has been created from the multiple imaging modalities. Such generation of a solid model form a mesh may occur according to a number of known manners.

Figure 3G:
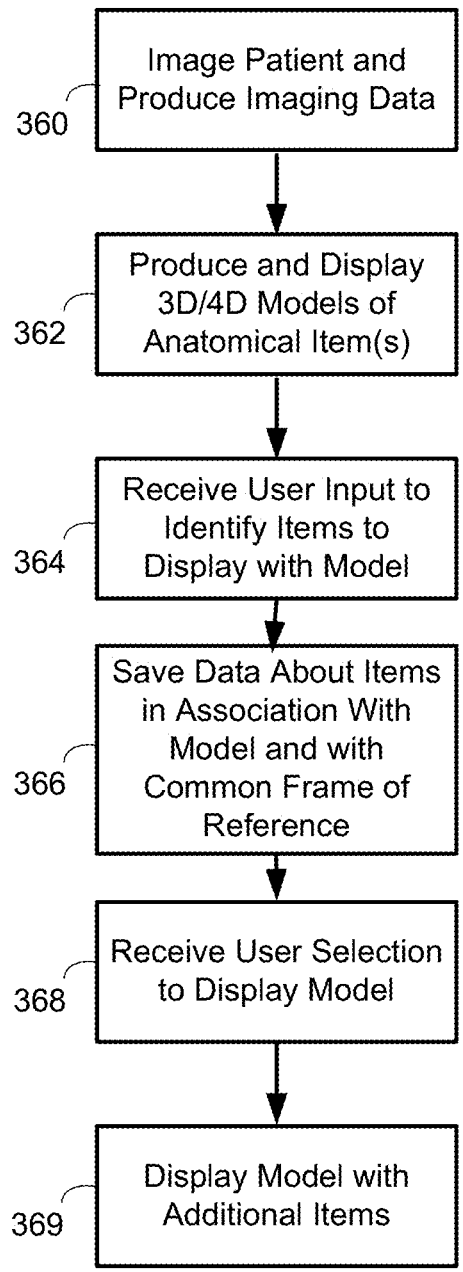

FIG. 3G is a flow chart of a process for coordinating metadata with a model of an anatomical item. In general, the process involves saving metadata along with a 3D or 4D model. The process begins at box 360, where a patient is imaged, and imaging data is produced from such imaging.

At box 362, 3D and 4D models of anatomical items from the imaging are produced and displayed. At box 364, a user input is received to identify items to display with the model. Such items are separate from the anatomical item, and may include geometric constructs and medical devices to be introduced into the model of the anatomical item and to thus annotate the model in a visual representation for a user.

At box 366, data about such extra items may be saved in association with the model and with a common spatial frame of reference. In particular, a file where the model is saved may reference a file where the additional data is saved, so that when the model is reopened at a later date, the additional items can also be opened with the model. The common frame of reference allows the items to be located at their same location relative to the model. For example, a spline through an open path in an organ may be reset in its proper location the next time the model for the organ is opened.

At box 368, a user selection is received to display the model. In this example, the user selection is made during a later session, perhaps after the user has shut down the visualization system or looked at other models with the visualization system. Because the additional data was saved in the manner defined at box 366, the model may be displayed with the additional items when it is later opened, as shown at box 369.

Figure 3H:
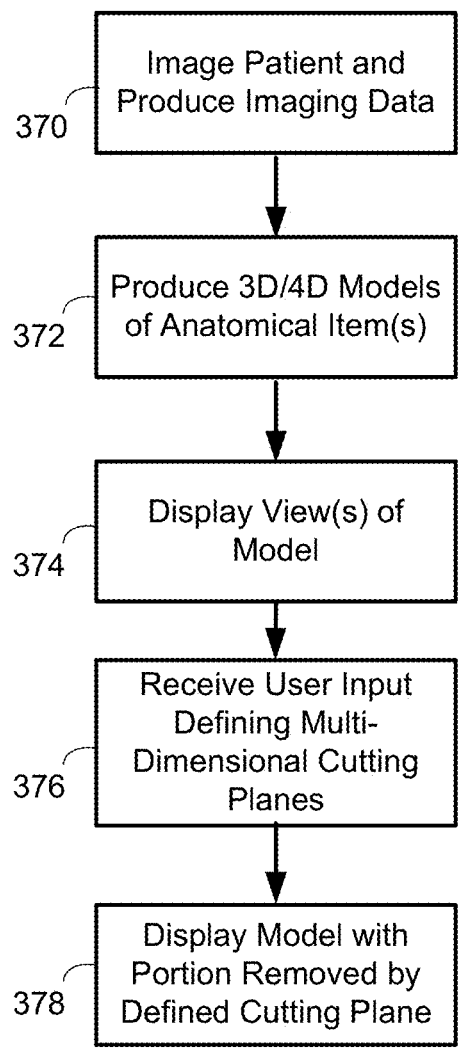

FIG. 3H is a flow chart of a process for cutting a model. In general, the process involves displaying a model that is being cut along multiple planes so as to provide a potentially complex view into an interior portion of the model.

The process begins at box 370, where a patient is imaged, and imaging data is produced for that patient. At box 372, a 3D and 4D model of an anatomical item or items that were captured by the imaging are produced. At box 374, one or more views of the model may be displayed. For example, an animated 4D view may be displayed adjacent to a non-animated 3D view of the model. In this example, both views may simply show the outer surface of the heart, and a user may want to get a better view of the inner portion of the heart. A single cutting plane may do an insufficient job of providing such a view because walls of the area may block a complete view of what a user would like to see inside the model.

As a result, at box 376 the user provides input that defines multidimensional cutting planes. For example, a patient heart may be displayed in a visualization system and a user may slide multiple representations over the displayed model of the heart so as to define three cutting planes that cut a corner out of the heart. At box 378, the model is displayed with the portion that was defined by the cutting planes removed. For example, if the user moved a cutting plane over a corner of an atrium of a heart, subsequent display of the model of the heart may show a part of that corner of the atrium removed. If multiple different models of the heart are shown (e.g., from imaging sessions that occurred at different times for the patient), a set of cutting planes can be applied to the second representation automatically in response to a user applying them to the first representation.

Figure 3I:
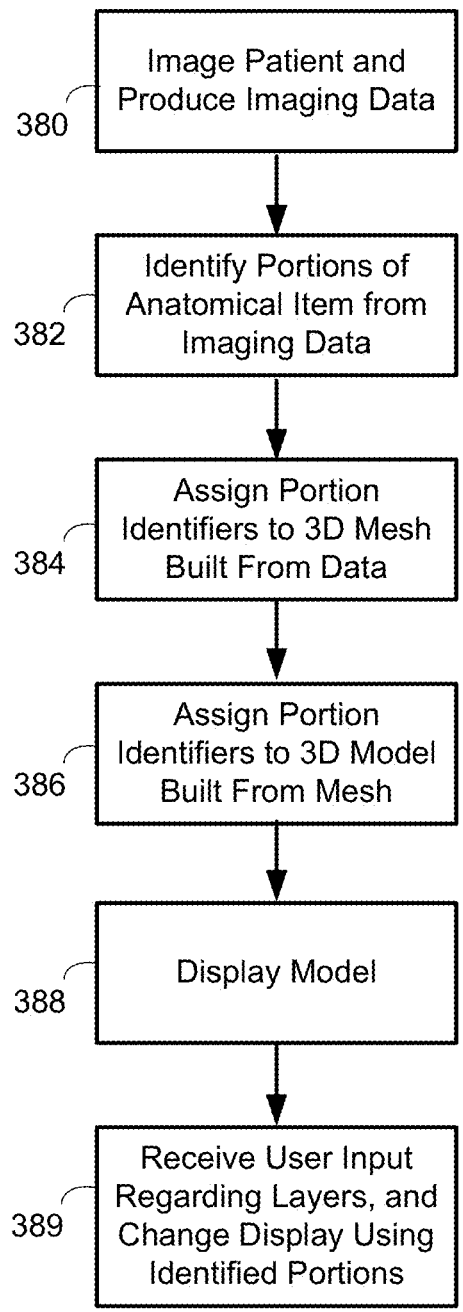

FIG. 3I is a flow chart of a process for building one or more models of an anatomical item. In general, the process involves breaking an anatomical item into sub portions and allowing a user to readily interact with those sub portions. For example, the parts of an organ such as the chambers of the heart may be identified when a model of the heart is built, so that a user may readily change colors up the chambers individually, or change other viewable properties of those chambers. Effectively, the portions of the heart are represented as layers that can be manipulated as individual groups, such as to turn them on and off visually, to color them, and the like.

The process begins at box 380, where a patient is imaged, and image data is gathered. At box 382, portions of an anatomical item from the imaging data are identified. For example, a system may be programmed to identify walls surrounding chambers in a heart from slices in the data, and may assign particular nodes in a mesh generated from the slices to layers for one or more of the chambers. As the mesh is defined in three dimensions, additional ones of the vertices in the mash may be defined according to a chamber to which they correspond, as shown at box 384.

At box 386, a 3D solid model is generated from the vertices in the mesh, and may inherit the portion identifiers that were assigned to the vertices that correspond to those parts of the solid model. For example, zones in the solid model may be identified and associated with particular ones of the layers.

At box 388, the solid model is displayed. Such display may include visually identifying the different portions of the anatomical item that were identified in the earlier steps, such as by providing different coloring or shading to various chambers of the heart. At box 389, user input regarding particular layers in the model is received, such as a user wishing to see only the heart cell layers to the exclusion of all other layers in the heart. The concept of layers in this example is similar to that of layers used in CAD and GIS applications, where certain layers can be turned on or off, or may be assigned properties according to all items that are identified as being in a particular layer such as a color property that changes all items in a layer to the assigned color.

Figure 3J:
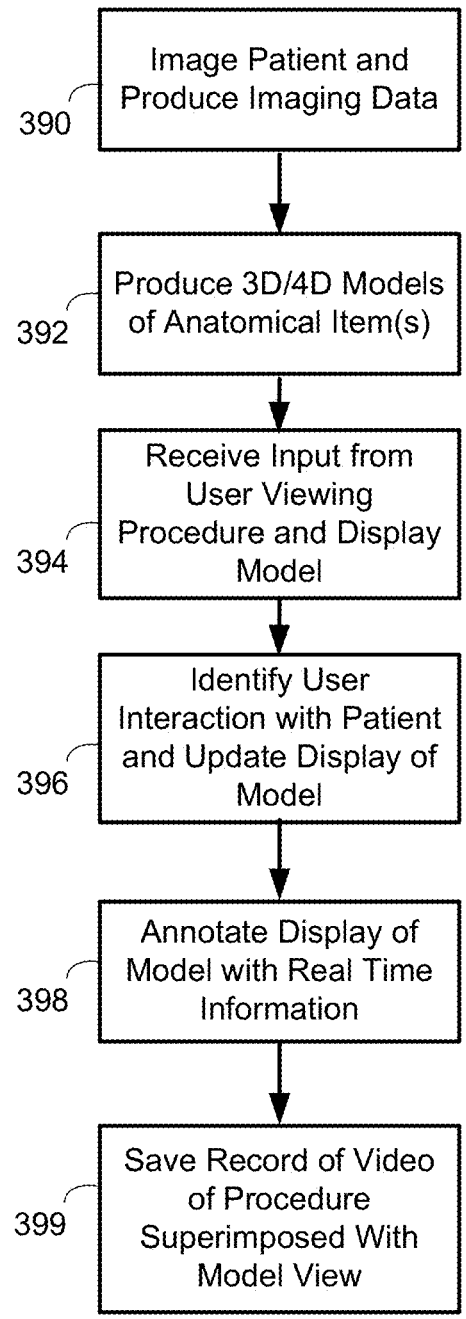

FIG. 3J is a flow chart of a process for providing visualization of an anatomical model. In general, the process involves providing a display of a model of an anatomical item while a user views the actual real-world representation of the anatomical item. In one typical example, a surgeon may be shown a model of a heart or other organ of a particular patient while performing surgery on that organ of the patient. In certain examples, the displays may be superimposed over the normal vision of the user, such as using hardware similar to that represented by the GOOGLE GLASS hardware, supplemented with an application to obtain imaging data from a hospital information system and to respond to physician voice commands for manipulating the model that is displayed.

The process begins at box 390, where a patient is imaged, and imaging data is produced from such actions, such as in the manners discussed above. At box 392, 3D and 4D models of one or more anatomical items in the imaging are produced. At box 394, input is received from a user who is viewing a procedure so as to display the model. For example, a 3D model of a human heart may be displayed that is cut vertically down the middle so that a surgeon can see the inside of the heart in the model. The heart that is displayed may be a model generated from imaging of the patient who is in front of the surgeon at that time.

At box 396, user interaction with the patient may be identified and a display of the model may be updated accordingly. For example, a patient vasculature and heart may be imaged and modeled in preparation for an angioplasty or some similar procedure. The depth of insertion of a surgical item, such as an angioplasty balloon may be monitored from outside the patient and such depth of insertion may be supplied to a visualization computer system that is displaying the model. A separate model of the device may then be displayed by such a system in relation to the model of the vasculature and heart, so that the physician may view, out of a corner of his eye and on a heads-up display, the relative progress of the medical device in reaching its ultimate destination. Such location information may be confirmed using other standard imaging techniques that are employed during a procedure, such as tracking an instrumented portion of the medical device using imaging technologies outside the patient.

At box 398, a display of the model is annotated with real-time information. For example, a system may display a numeral representing a depth of insertion of a medical device into a patient (e.g. in inches). Similarly, as a physician introduces the medical device and interacts with walls of the heart, similar interaction may be simulated in the model, and annotations may be provided on the heads-up display to indicate to the physician the level of stress or strain that is being applied at that moment to the tissue. Other annotations may also be provided to assist the physician, such as heart rate and blood pressure that is currently being measured for the patient. In addition, notes from assisting staff may be displayed to the physician using a notifications interface that is provided with an operating system for the heads-up display.

At box 399, a record of a video of the procedure is saved along with the superimposed model view so that a representation of what the physician saw during the procedure may be maintained. Such a recording may be provided for training to other physicians, may be studied by the physician himself to improve his technique, or may be used in multiple other manners. The video may show a camera view from the front of a pair of glasses, such as GOOGLE GLASS, worn by the physician, and in one corner of the recorded video, a display may be shown representing what the physician was presented by the visualization system at the same time as the physician was viewing the procedure (e.g., the model of the organ and/or alphanumeric and graphical annotation data).

Various processes have thus been described to indicate uses for an imaging system that presents models of anatomical items, like a heart and vasculature, in 3D and 4D presentations. Such processes may be used by physicians during procedure, by physicians in preparing for a procedure (e.g., to identify a proper size for a medical device to be used with a particular patient), by physicians in explaining to a patient his or her pending procedure, by a physician or salesperson to train another physician or to explain the benefits of a particular device or procedure to the physician, by medical device manufacturers at conferences to explain new procedures, and for a variety of other general uses.

The following discussion addresses more generally virtual prototyping tools for use in medical device interactions, including a user interface for a computer-based visualization system that generates views of medical devices in relation to parts of a human body and allows a user to manipulate such virtual devices and receive both image-based and alphanumeric data-based feedback about such manipulation, such as by seeing a "heat map" display that changes the color of displayed tissue as a function of forces exerted on the virtual tissue by the virtual medical device, in addition to seeing a table that provides alphanumeric descriptions of those forces (as just one example).

The system may include a 3D touch table VR holographic imaging system or a commercially available VR system, such as a system from zSpace of Sunnyvale, Calif., which may be provided with additional programming to carry out the operations described above and below. Features of such a system may include: (a) integrated file loading for image sequences and triangles meshes; (b) support for loading and interacting with multiple meshes; (c) support for loading multiple meshes inside of a single linked coordinate frame; (d) support for multiple splines inside environments; (e) support for loading and saving splines to disk; (f) customization tools for changing the color of meshes/splines; (g) camera path support for flying the view windows along splines; (h) video recording functionality that supports external stereo viewing on a 3D TV; (i) real time iso surface extraction from loaded image sequences; (j) project loading/saving for saving the entire state of the program; (k) view resetting if meshes get lost; (l) device sizing option for setting a radius of a device to understand how it fits in the geometry; (m) interactive visual feedback and widgets that make the interface intuitive, even for novice users.

Additional functions that such a programmed and implemented system may include are: (a) loading FEA data into both systems; (b) per-vertex coloring of meshes; (c) three views (sagittal, coronal, transverse) in the upper left corner of the projector screen that are stationary and do not scale with user controlled zooming; (d) viewing and controlling/manipulating 4D anatomical data sets; (e) ability to rotate cutting planes; (f) ability to toggle cutting planes on/off; (g) ability to toggle bounding boxes on and off; (h) measuring capabilities, such as average distance to center of a spline (e.g., to tissue surrounding the spline in a representation of a spline in a human organ) and center points relative to a mesh.

To that end, the following figures discuss software and hardware used in one example of an immersive multi-touch workbench setup, and provide an overview of one configuration and example settings for various system components. The description discusses selected system components and provides procedures for configuring the system. A first section describes the general system setup, detailing the operating system settings. A second section details the camera hardware and software to track the user's head position. A third section describes the multi-touch overlay that is used to provide touch input to the system. A fourth section includes a description of the custom model viewer software.

General System Setup: Different examples of the present subject matter can include various touch hardware setups. One example setup includes a projector, and various setups can include two screens or a third screen (monitor). The description here can serve as a guide, and individual configurations may benefit from customized tuning. This section describes the computer and peripherals along with relevant Windows OS settings (though the system may operate using a variety of operating systems). There are three video outputs in the example system: (a) a projector displaying on a vertical screen; (b) a large-scale flat monitor (e.g., LCD) displaying on a horizontal touch surface; and (c) a computer monitor positioned to the side of the other displays and intended for desktop use. Appropriate video cards may be used for generating such graphics in a coordinated manner Head Tracking Cameras and Software: An example of the head tracking subsystem includes four IR cameras mounted above the system, a USB hub connected to each camera, and the software that runs the cameras. This system identifies the location of the user's head by tracking reflective markers affixed to the user's head, such as on a headset worn by the user. In one example, the markers are affixed on the head using eye glasses. The system streams the position and orientation of the head position to the model viewing software. Accordingly, the software can be running before the start-up of the model viewer software. The start-up procedure for this software is executed after it has been calibrated. Additionally, the cameras should be in a stable position and should not need readjustment. However, over time it is possible that due to the set up being bumped, or the loss of the main configuration file, this system may need to be calibrated.

Figure 4A:
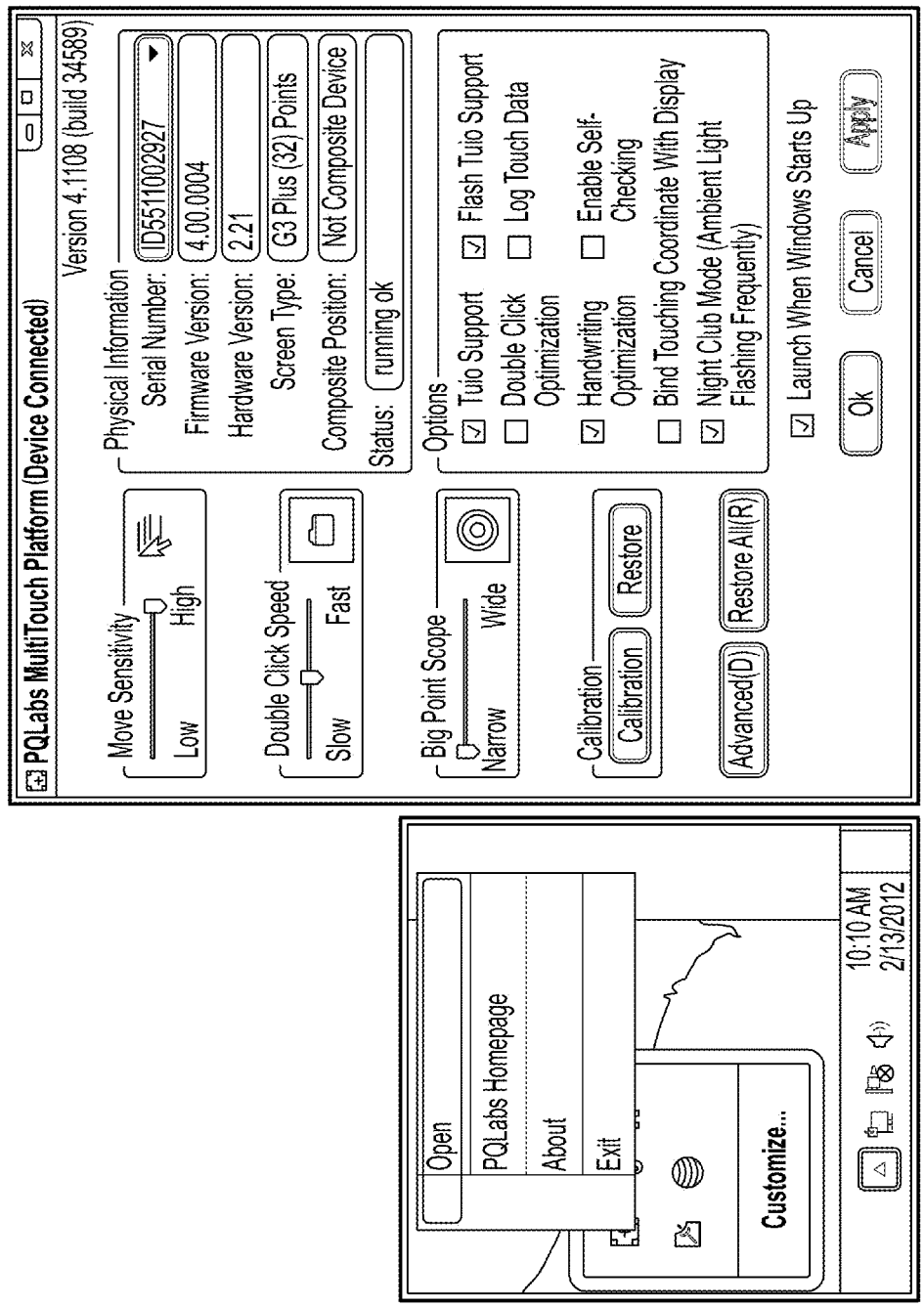
FIGS. 4A to 4L are representation of a user interface for a visualization system for use with parts of a patient's body, such as organs.

Multi-Touch Overlay: A touch overlay sits on top of large horizontal TV display and detects touch contacts and resends them to a computer in a similar way that the head tracking data is streamed to the computer. It connects to the computer via a USB cable and has a separate cable to power it. In addition to sending the touch input info to the model viewer software, the touch overlay also interacts with the operating system, which is why icons and cursors pop up when touching the surface even when not running the program. In this way, the input can also act like a mouse for the system. The options for the overlay software can be accessed through the tool tray menu in the lower right of the screen as a "cross-hair" icon, as shown in FIG. 4A.

Figure 4B:
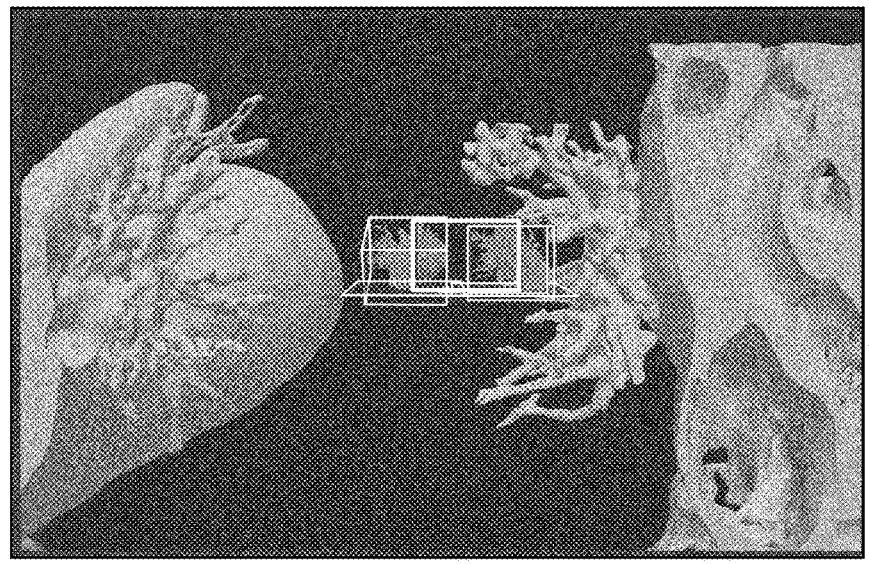

Model Viewer Software: In one example, model viewer software supports loading of two different types of data (that are typically linked to each other): (a) 3D triangle meshes (typically a Standard Tessellation Language {STL} file format); and (b) sequences of medical imaging files that define volumes (DICOM/png image stacks). The system supports loading an arbitrary number of image stacks and/or triangle meshes into the software. When the software opens, a default set of data is loaded. New data can be loaded to replace these existing sets. The system works by supporting multiple "frames", where each frame can contain multiple triangles meshes and a single linked image stack (i.e. volume). These are called "frames" because all the data loaded in them shares a single coordinate frame origin. Thus, when manipulating this frame, all the contained meshes and the image stack are manipulated together. Each of these frames is visually depicted by the red bounding box that shows its extents. FIG. 4B shows an example of such multiple frames, indicated by red bounding boxes, each containing a 3D heart geometry.

The model viewer software is effective when the frames contain both triangles meshes and imaging stacks together. However, for this to work, these two sources of data are to be registered so that they line up properly. The software accomplishes this by making certain assumptions about the coordinate frames of the triangles meshes, and conventions in how the image stacks are mapped into 3D. The following paragraphs outline these assumptions and conventions. There are multiple ways to meet these conventions. For example, in the export process of the software being used to segment the geometries, they can be kept consistent. However, with existing data that does not meet the assumptions, to load the data, a piece of software that is helpful in changing coordinate frames is the free 3D triangle mesh software called MeshLab.

Figure 4C:
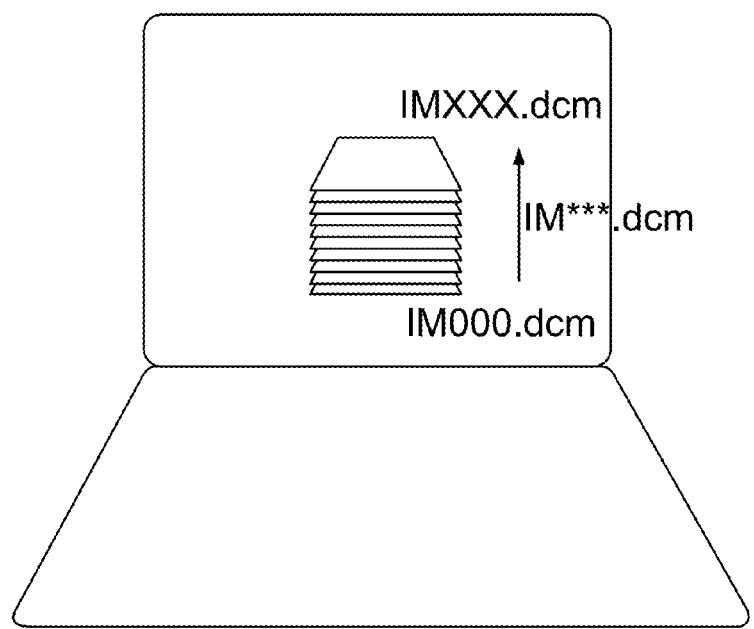

The global coordinate frame for the entire virtual environment is defined by a general Cartesian coordinate system with the positive Y-Axis points upward. When triangles meshes are loaded in, they will default to match this orientation (their local frames can be rotated afterwards though), as shown in FIG. 4C. That figure shows the order in which the series of Dicom slices are loaded, the first image (here shown as 000) as being loaded at the bottom of the volume, and the last image (here labeled XXX) loaded at the top. This order should be maintained to properly orient the volume with the mesh. An image stack is assumed to stack in the positive Y-Axis direction. Thus, the positive Y-direction of a loaded mesh should match the direction associated with increasing sequences in the image stacks.

To register meshes and image stacks, there are two distinct approaches the software can use. The first approach (basic) is used when the extents (i.e. bounding boxes) of the mesh and of the image stacks are exactly the same. The second approach (advanced) is used when the extents do not match up and additional information must be input to register the data properly. These two methods are distinguished by the order in which the data is loaded. If triangle meshes are loaded first, and then an image stack is prescribed to it, the basic method is used. If the image stack is loaded first, then the more advanced method is used to set up the volume properly, after which a mesh can be loaded in the registered coordinate frame. These two processes are detailed in the figures below.

Figure 4D:
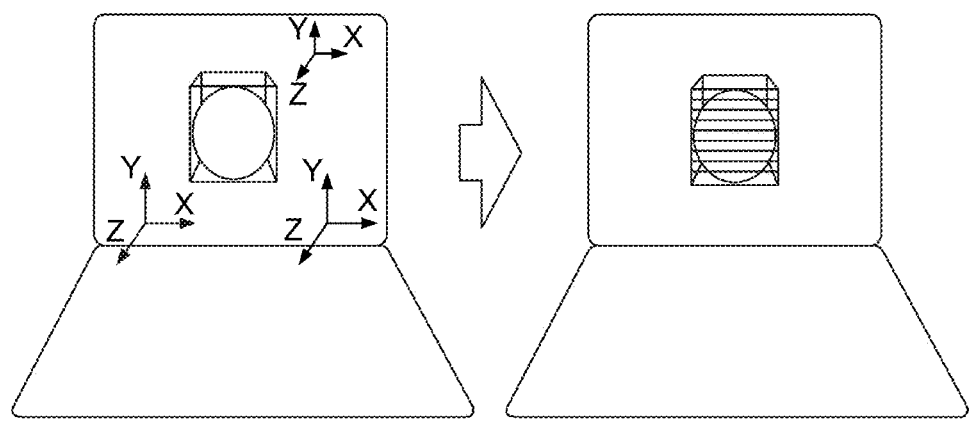

FIG. 4D shows the basic loading process. The mesh is defined first (in the left image)—its local coordinate origin can be essentially anywhere and its extents will be indicated by the red bounding box. After a mesh has been loaded, an image stack can be applied (shown in right image) and will fit to match the extents exactly. This strategy will only work if the meshes extents exactly match the loaded volume's extents.

Figure 4E:
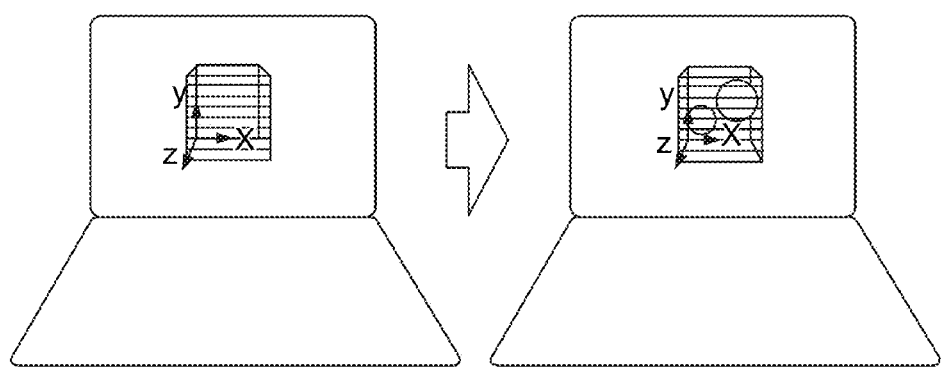
Figure 4F:
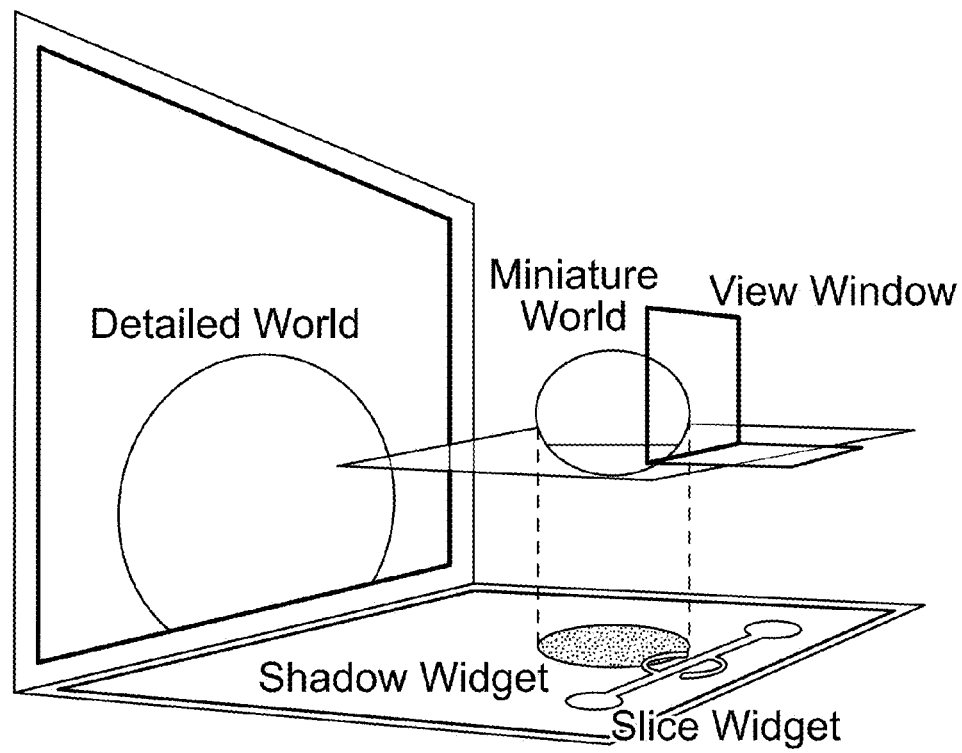

FIG. 4E shows the advanced loading process. The volume is loaded—its local coordinate origin is fixed to be in the back-lower-left (minimum) corner of the bounding box (which must be defined via additional input). Additional meshes can be loaded and if they share this common coordinate frame, they will be properly registered. This technique is helpful if only a subset of the image stack was segmented.

Program Controls (Touch Hardware):

The model viewer software uses a World-In-Miniature (WIM) metaphor to navigate and interact with the world. The WIM serves as a smaller map of the world that floats above the table surface, as seen in the figure below. The current position inside the world is indicated relative to the WIM by the "View Window." The larger scale version of this view is shown in the "Detailed World" behind the WIM. Finally, two widgets are projected on the table surface that the user interacts with. First, the "Shadow Widget" is a vertical projection of the WIM down onto the table. Second, the "Slice Widget" is a vertical projection of the view window onto the table. The metaphor is shown graphically in FIG. 4F. The Shadow Widget is used to directly control the WIM itself, either to position and scale it to different location or size, or to rotate and orient it to view the world from a different direction. A set of gestures is used to perform each of these actions, as seen in the figure below. These gestures can be enacted anywhere on the table surface (except the Slice Widget). These gestures can be used on individual frames or across all frames by interacting on top of the shadows of objects or elsewhere on the screen.

Figure 4G:
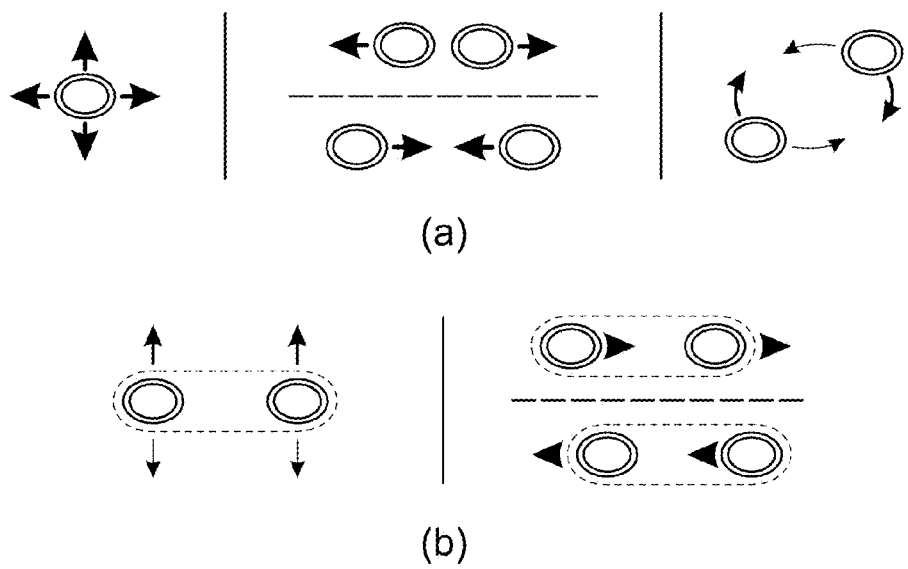

FIG. 4G shows (a) gestures for translating, scaling, and rotating the WIM in the plane of the table surface, and (b) gestures for tilting and rolling. The Slice Widget can be used to directly control the current position and scale of the detailed world. The green line projection on the table provides a set of handles to grab the ends of the floating view window. These handles are indicated by the blue circles at the ends of the Slice Widget, as shown below. Each of these handles can be independently grabbed and manipulated to change the position of the View Window. To change the zoom level, the window can be scaled to be bigger or smaller. The yellow line indicates the current viewing direction into the detailed world. The vertical height of the View Window can be adjusted by moving the thumb near the double-sided arrow indicated in red. By pressing and holding the rotating arrows in the center of the Slice Widget, the WIM can be spun around by moving a second finger on the table surface while fixing the View Window in place to flip the world around to see from the other direction. The lock icon near each handle can be used to change the viewing properties of the WIM by tapping the lock icon to cycle through the options. In the default mode, open lock, the WIM will only appear when the user is interacting with it. In the locked mode, indicated by a closed lock, the WIM will always stay visible. In the hidden mode, indicated by an empty circle, the WIM will always be invisible, even when interacting. A fourth mode will always hide the zoomed in view and only show the WIM.

Figure 4H:
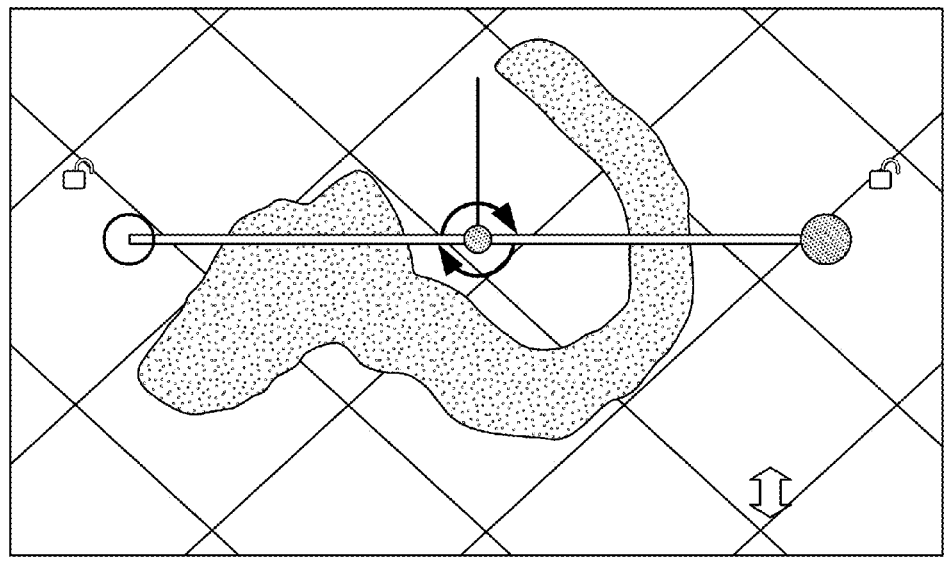
Figure 4I:
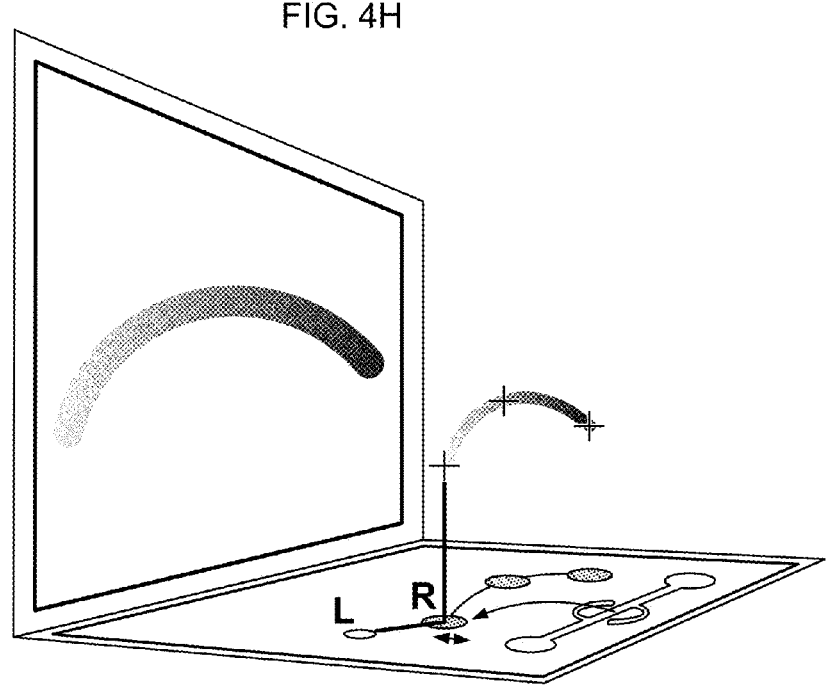

FIG. 4H shows a slice widget. Handles (circles on both ends of the line) are used to position the view window inside of the miniature world. The height of the horizontal slices can be adjusted up or down by dragging the thumb near the double arrow in the lower right of the figure.

A feature is available for specifying curves and volumes inside patient anatomies, i.e., in particular anatomical items. Placing a finger down on the center of the Slice Widget and dragging out from it will create a 3D point. The point is moved in a plane parallel to the table surface by dragging it around the table. To change the vertical height of the 3D point, a second finger, usually in the opposite hand, is pressed on the table and a "virtual string" is connected between the user's fingers and the 3D point floating above the table. Bringing the two fingers together loosens the string, allowing the 3D point to go higher. Similarly, moving the two fingers apart lowers the 3D point. Finally, with two fingers pressed in this manner, a third finger, usually a thumb, moved vertically on the table, will inflate or deflate the curve at this point to encompass a volume. Such a gesture is shown graphically in FIG. 4I. There, points are specified in the 3D space relative to the miniature world. Multiple points are combined to form curves and may be expanded via an additional touch gesture to define a generalized cylinder.

The software described herein can be operated on the zSpace hardware platform. The main input device there is 6-degree of freedom wand instead of a 2D touch input surface. This wand's translation and rotation are both tracked, and all the manipulation described in the touch hardware is replicated by using the wand combined with three buttons on it. To retain the concept of a "table" without a second display, the horizontal table surface is moved backwards beyond the angled zSpace display and exists only in virtual space. Additionally, the world-in-miniature visuals and interactions used in the touch enabled hardware setup are removed in the zSpace version. Only the miniature is shown and manipulated by the user, and no view window is used.

Figure 4J:
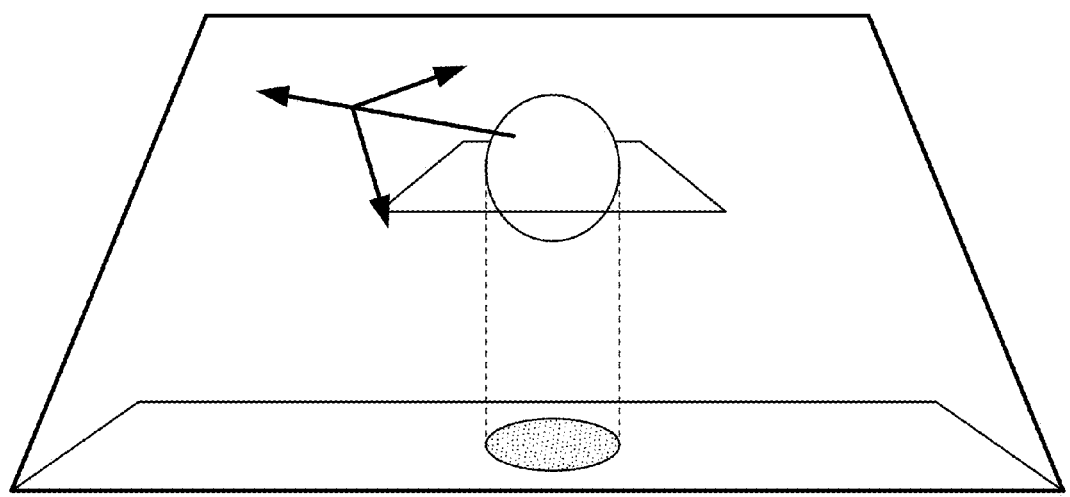

FIG. 4J is an illustration of the model viewer software components on the zSpace hardware. The vertical screen rests at a 60 degree angle from a table on which it sits. The virtual table is drawn behind the window and the shadows are projected on it. The stylus device, indicated by the coordinate frame and yellow line, are used to interact with the virtual environment. The tracked stylus (or wand) is used as a virtual cursor to interact with the model viewer software. It can be used to simulate a touch event on the table surface by pointing it down and intersecting a ray with the table. When pressed, this button combined with stylus motion will simulate a touch event on the virtual table. In this way, all single-point interactions used in the touch hardware can be performed. In addition to this basic capability, other more advanced 3D interactions (that would otherwise require more than one touch point) are supported. A large main button on the stylus serves as a "grab" button. By pointing the stylus at the bounding box of each frame and clicking the grab button, the mesh can be moved in a one-to-one mapping following the stylus' position and orientation. There are also other features that can be manipulated with the grab button; for example, the horizontal slice can be grabbed and moved up or down to change the view depicted in the shadow on the virtual table. There is also a vertical "wing" on the left side of the virtual table that can be moved forward, backward, upward, and downward to change how far away the vertical clipping plane is. The grab button can be used to grab onto the location of controls points of splines to position them in 3D.

The right button on the stylus serves as a "scale" button. By pointing at a bounding box followed by a clicking and dragging action, the button can be used to scale the data (e.g., meshes or solid models) contained in that bounding box's frame either up or down by moving away or toward the center of the box. The scale button can also be used in this same way to change the radius of the tube created by the spline. This scale button also has an additional feature that can be used to rotate the virtual table upward, with a hinge at the front end of the zSpace display. This is useful for interacting more easily with the table surface, which is helpful when using the 2D table widgets described later in this document. This can be performed by pointing the stylus down at the table, pressing the scale button, and moving the stylus upward. Another function of this button relates to the "wing" mentioned earlier. By clicking on the wing and pressing this button, the wing can be rotated to change the angle of the clipping plane so that is it not perfectly vertical.

A third button on the left of the stylus serves as a "cursor" button. Clicking on this button will create a new 3D cursor for a spline in the nearest frame. This works in the same way as the dragging operation described above in the touch hardware. After clicking, the cursor can be positioned and will remain stationary after the button is released.

Figure 4K:
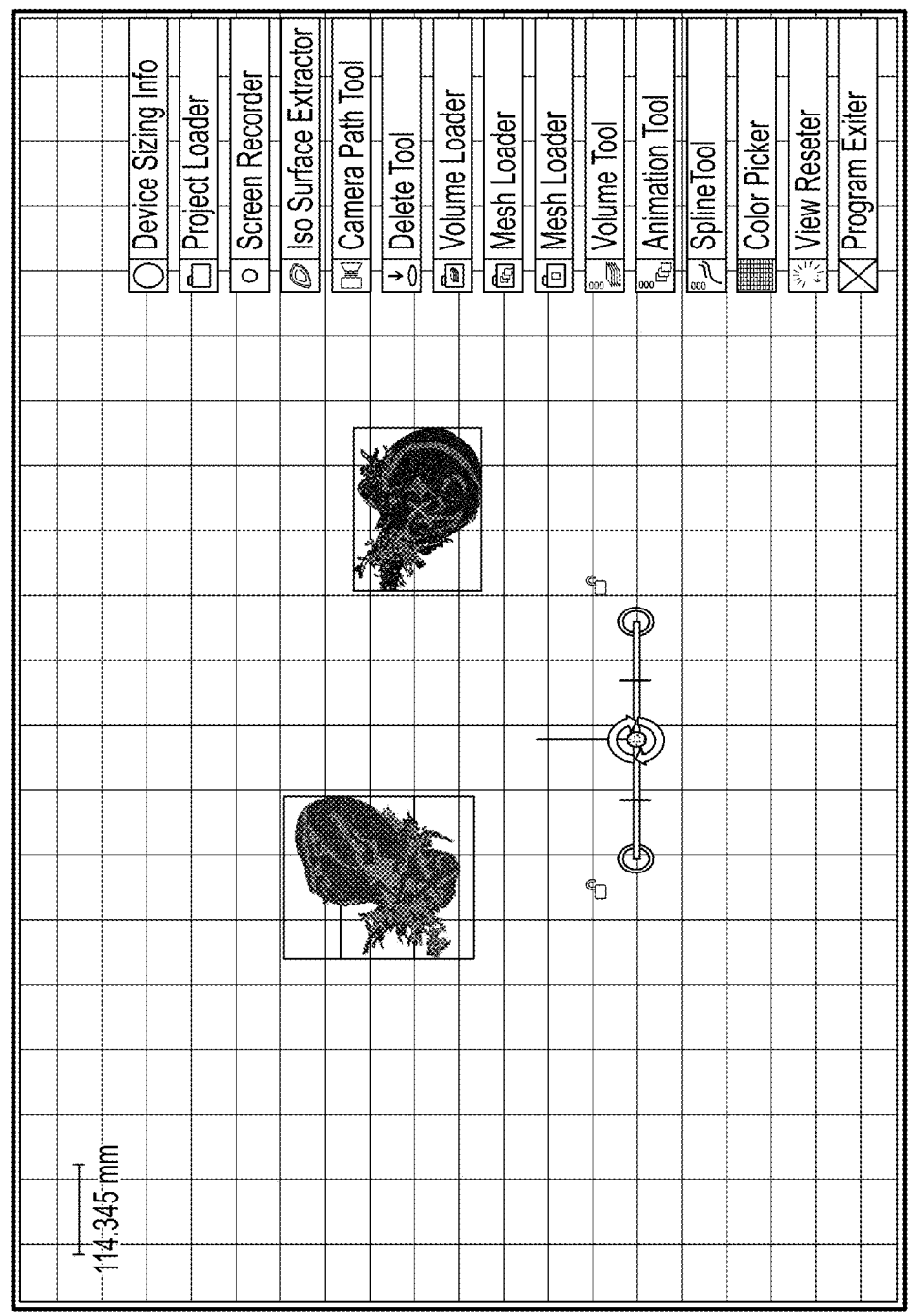
Figure 4L:
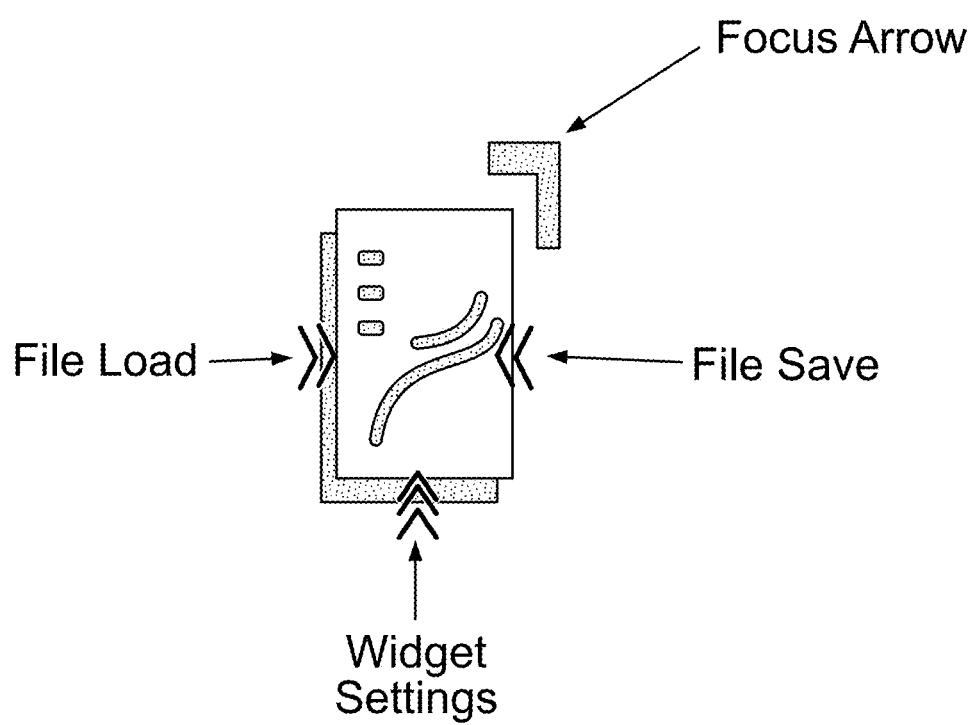

FIG. 4K shows a display of a virtual table with drag-able touch widgets docked on the right of the screen. Each of these widgets can be moved out onto the table and used to change settings of the virtual environment. Many additional features are available to the model viewer software, including the ability to load and save files or change the visual settings of the virtual objects. The software makes use of a touch widget metaphor for implementing these features. A set of widgets is docked on the right of the screen. Each of these can be dragged out onto the virtual table (via touch or stylus interaction). These widgets can then be interacted with to perform various actions. Often these actions are dependent on a widget's location on the virtual table. For example, if the widget is located on a specific shadow of a mesh, it will change the settings for that specific mesh. The following sections will go through each of these widgets in more detail, describing what they do and how to use them.

In addition to the visual square icon representing the touch widget, each widget can have four different features that are consistent across all the widgets in their functionality. These four features are labeled in FIG. 4L. Each of the arrows can be clicked on and will be expanded to contain more controls. If the widget contains a focus arrow, then the location indicated by the tip of the arrow corresponds to either which data elements are modified by changing the settings or corresponds to where the file loaded will be located upon finishing the load operation.

The Program Exiter widget is used to close the program. Simply drag it out onto the table and double click it to exit the software.

The View Resetter widget is used to reset and center the currently loaded frame plus the view window. It is useful for when the virtual objects get lost, typically caused by extraneous inputs on the touch surface. It will reset the scale of the objects so they fit on the screen well, and array them horizontally along the center axis of the virtual table. The Color Picker widget is used to set the color of individual meshes inside of the frames. After it has been placed on the table, it will display a paint brush icon combined with a circular color palette. The mesh with its center closest to the tip of the paint brush will be selected. After selecting, a touch point inside the color palette can be used to drag and change the color applied to the mesh.

The Delete Tool widget is used to remove/unload existing frames (i.e. meshes and image stacks) from the software. Simply move the focus arrow on top of the frame to be deleted and double click the widget to delete it.

The Spline Tool widget is used to modify, load, and save 3D splines (curves) that have been created using the earlier described spline generation interactions. The file type used to hold the spline information is a comma separated value (csv) file that can easily be read into spreadsheet software. It has two sections. The first section lists the locations of the exact control points used to create the spline. The second section lists the points resulting from evenly sampling the mathematical representation of the spline curve. Each of these is listed using four columns—the first three columns define the X, Y, and Z position of each point. The fourth column defines the radius of the spline's tube at that control point. To save a spline, the widget can be dragged so that focus arrow selects a curve on the table. Then, by expanding the save window and selecting a directory, a csv file will be created with an auto-generated file name time stamped to when the file was created.

To load a spline from disk, drag the widget into the frame where the spline is to be loaded, expand the load window on the left of the widget, and select the .csv to load. The spline will be recreated in this frame and can then be modified. There is also a set of widget settings that can be used to change the behavior of splines, and information associated with each spline, that can be seen by expanding the arrow on the bottom of the widget.

A description of these elements is as follows: (a) total Spline Length—Reports the entire length of the currently selected spline; (b) current Segment Length—Reports the length of the distance between the last control point and the previous control point; (c) Avg Distance to Wall—Reports the average distance from the center of the spline to the nearest boundary found radially outward from the spline. This value is computed on demand when the button mentioned below is pressed; (d) Frozen (Check Box)—If checked, the spline will be locked into place and controls points can no longer be manipulated; (e) Trailing Buffer (Check Box)—If checked, only the last three controls points of the spline will be modifiable, acting as a trailing buffer. This is helpful if the spline contains many points, such that they become difficult to individually select due to clutter; (f) Center Spline (button)—When clicked, the entire spline will be centered relative to the surface that surrounds it; (g) Compute Average Dist (button)—When clicked, the average distance from the spline to the nearest wall will be found by searching radially along the spline. This value is reported in the above mentioned text box; (h) Generate Radial Spline (button)—This button is used to generate a new spline that follows the exact shape of the surface. It uses an existing spline to seed the generation of the new spline. The seed spline must intersect the plane of the vertical wall surface. The point where this spline intersects is used to shoot rays in the plane of the vertical surface and control points are positioned at the intersection of these rays. For example, if a spline was placed that followed the center line of an artery, and the view was rotated so this spline is clipped at the vertical plane, after this button is picked a new spline that lies in the vertical plane will be created that follows the contour of the inside of the artery.

The Animation Tool widget is used to control the settings for temporal datasets that have been loaded into the software. This includes both 4D meshes and 4D image stacks. After a frame has been loaded with either of these types of data, this tool can be dragged onto its shadow and the following information/settings are available: (a) Total Animation Time—The current time in seconds to complete the entire sequence of loaded animations, change this setting to match the desired animation speed; (b) Number of Volumes—Reports the number of volumes in the currently loaded volume sequence of the selected frame; (c) Animation Interval Time—The time step between consecutive volumes in the sequence. Total Animation Time=Number of Volumes*Animation Interval Time; (d) Mesh Animation Time—Sometimes individual mesh sequences inside of the frame have different timing than the other meshes (or the loaded volume sequence). This setting controls the timing for the individual mesh sequence that is closest to the focus arrow. By default all loaded mesh sequences match the total animation time, however it can be changed by modifying this value; (e) Number of Meshes—Reports the number of meshes in the mesh sequence that is closest to the focus arrow; (f) Mesh Animation Interval Time—Analogous to the "animation interval time" above, but for the individual mesh sequence; (g) Playback Speed—the speed at which the animation is played, defaults to one for real time playback, but is adjustable to speed up or slow down the animation. In addition, this widget has an additional time line window that can be moved around. This time line has a play/pause button attached to it, to start or stop the animation of the frame currently selected. The time line shows an indicator of how far in the animation the current display is. The time line is interactive, by dragging along it the current time step can be changed.

The Volume Tool widget is used to configure the dimensions of loaded image stacks, as well as several controls for changing the visualization settings. This tool is used to properly set up the coordinate frame located at the minimum corner of the image stacks 3D bounding box (as described in section 5.3). As a user changes the input, the bounding box of the volume will update. It will continually resize so that it does not become so large or small it can't be seen anymore. Despite this, the bounds of the box are changing (and a scaling factor is being changed to account for this). The bounding box must be set up correctly so that subsequent loaded meshes are in the correct position and scale. The settings in this section should be configured to match the units/coordinate frame in which the subsequent meshes to be loaded are defined. The available settings are:

The Volume Scale to Meters widget is used to set the units that the meshes/volume are using, when multiplied by this scale factor, the units should be in meters. For example, if the meshes and volumes were exported using mm as their units, then this scale factor should be set to "0.001". This factor is in turn used to ensure the display outputs are reported in their correct unit (which would be unknown without this factor). Various check boxes operate as follows: (a) Texture from Volume turns on/off 3D texturing on the meshes. If on, the image stack will be treated as a "block of marble" and the colors contained in the volume defined by the stack will be mapped onto the meshes surface; (b) Show Solid Slice turns on/off solid modeling for the selected mesh. If on, the mesh will be treated as a solid object that has a defined inside and outside, when clipped into, the inside will be rendered flat at the clipping plane, such that the inside is hidden from the clipping (i.e. back faces are not visible). This should only be used on watertight, well-defined meshes where the front and back faces are all consistent; (c) Show Shadow Slice turns on/off a shadow representation of the current horizontal slice through the meshes; and (d) Texture WIM turns on/off a 3D texturing on the WIM, a 3D texture has been set.

The Device Sizing Tool widget is used to configure the device sizing tool which is available for measuring out diameters in the virtual environment. The red line on the view window's shadow can be moved to directly control this virtual device radius. In addition to this basic control, this widget allows precise setting of the size. The following settings are available: (a) Freeze Device Width (check box)—When checked, the device will be frozen at its width and cannot be modified anymore; (b) Always Show Device (check box)—When checked, the circular device indicator will always be shown, instead of the default behavior which is only shown when it is interacted with; (C) Never Show Device (check box)—When checked, the circular device indicator will never be shown; (d) Device Width (mm)—Allows the user to precisely set the device width (diameter) in mm.

The Camera Path Tool widget is used to animate a camera (i.e. the view window) along the path of a spline. First, a spline must be created in the desired environment. Then, this widget can be dragged onto the shadow of a spline. After positioned on a spline, the camera can be controlled using an additional set of buttons. The left-most button (the right angle) is used to square up the view window so that it is perpendicular to the direction of the spline. After square up, the "play" and "reverse" button can be pressed to start the camera along the path in either direction. If the opposite one is pressed when it is animating, the camera will pause. Additionally, the right most buttons can be pressed to either speed up or slow down the motion of the camera.

An Iso Surface Extractor widget is used for performing real time extraction of iso surfaces from image stacks. This may be helpful if a new image stack is imported, but no other software has been used to segment a mesh from it yet. This widget will perform a simple marching cubes iso value segmentation routine to extract the surface at a particular value. The value it uses is set by pointing the focus arrow at the display image slice on the table. The value immediately under the tip of the arrow will be used as the iso value and a surface representing the boundary at that value will be extracted. The following additional controls are available: (a) Active Extract (check box)—If checked, the iso surface will be continually extracted each time the widget is moved. Due to the fact that the computation can be intensive on very high resolution image stacks; (b) Invert (check box)—If after extracting, the normals on the mesh are incorrect (i.e. the back faces should be the front faces or the lighting looks incorrect), this check box can be used to switch the directions of the normals so the next extraction is correct; (c) Select (button)—If pressed, the iso surface will extracted as described above. Only one iso surface can exist per frame, if an existing iso surface is in the frame, it will be replaced.

A Screen Recorder widget is used to capture video from the screens for replaying externally after an interactive session. The file names are auto-generated depending on the timestamp, additionally, they will have a modifier in their name (left, right, or table) to indicate if they are the left eye of the stereo screen, right eye, or a capture of the table surface. To capture interaction, the rendered frames are encoded into a video. This encoding has an associated frame rate at which the video will be played back. For the video to play back at the proper real time speed, the frame rate of the encoding should ideally match the frame rate of the render graphics. A close default value is used, but depending on what is being recorded and other system load, this value may change. Thus, ideally the video frame rate should be set manually to an appropriate value. This frame rate control and other related settings are available via the widget: (a) Average FPS—This field will report a running average of the current rendering frame rate, this is ideally the value that should be entered into the encoding FPS field. However, this value will decrease after recording is started, as the rendering time adds significant additional load to the system causing slow down; (b) Record in Stereo (check box)—If checked, both the left and right eye views will be saved out to two separate video files. Third party software (e.g. Bino) can then be used to compose these two video files and play it back in stereo. If unchecked, only the left eye is saved; (b) Record Table (check box)—If checked, a video file will be created that captures the graphics rendered on the table surface; (c) Encoding FPS—A modifiable field that tells the video encoder what frame rate to encode at, ideally this should match the value reported in the Average FPS field (note this value will decrease after recording is began though); (d) Start/Stop Recording (button)—When clicked, the video recording will start. When unclicked, the recording stops and the videos are saved to disk.

The Mesh Loader widget is used to load new triangle meshes into the software. These triangle meshes can be added to existing frames, or new frames can be created to contain their own separate meshes. Using the expanded load window, a file can be browsed to and selected, upon selection the file will be read and the mesh will be displayed. Only a single file can be loaded at a time, to load multiple meshes, load each one sequentially. The main supported file format is STL, which most CAD packages support exporting to. Additionally, many other triangle mesh formats work as well, for example Wavefront OBJ files.

The Temporal Mesh Loader widget is used to load sequences of triangle meshes that are temporally consecutive. A sequence is loaded simply by specifying the list of triangle mesh files to load (where the order of the filenames is temporally consistent). This widget works almost identically to the "Mesh Loader", however in the load window multiple files should be selected that define the sequence, instead of just one.

The Volume Loader widget is used to load image stacks (i.e. volumes) into frames. Exactly one image stack (or sequence of image stacks) can be loaded per frame. If the stack is loaded into an existing frame it will replace any existing image stack, otherwise a new frame will be created. The load window can be expanded and a list of files can be selected that contain the image stack to load. Dicom images are supported, but most other image formats are also supported, png files (that also support color) typically are more robust. The images will be loaded in the order they are listed in the file browser (which is alphabetically sorted). The arrow at the top of the file browser window can be used to reverse the ordering of the filenames. Additionally, there is also a "bookend" feature, where the starting file and ending file can be selected, and after pressing this "bookend" button at the top, all in between files will be selected. Finally, temporal sequences of image stacks can be loaded with this widget as well. To do this, each stack should contain the exact same number of images, and the images that compose all of the sequential images stacks should be located in a single folder, such that the first image in a subsequent stack immediately follows the last image in the previous stack. Then using the additional settings, the interval of how to break up this large list of files can be specified. The specific additional settings are as follows: (a) Load Empty (button)—If pressed, a new frame with an empty volume will be created; (b) Temporal Volume (check box)—If checked, the list of files will be loaded as a temporal sequence, as described above; (c) Slice per Timestep—The interval that distinguishes sequential image stacks from one another, for example if 200 images were loaded, and there were 10 sequential volumes in it, 20 should be entered here.

The Project Loader widget is used to save out the entire state of the system as it currently is. This is helpful if multiple meshes and volumes have been loaded, and different settings have been applied, and you wish to save it for displaying at another later time. By expanding the save window and selecting a directory, a .proj file will be saved containing all the information needed to reload the software in the exact same state as which it was saved. This .proj file is in plain text and can be examined in a text editor if you wish to change some individual settings manually. To reload a saved project file, expand the load window, browse to it, and select it. It may take a few minutes to load all the files linked in this project. For the project load to be successful, the files that were used when the .proj was saved must reside in the exact same location. Additionally, sometimes certain filenames may break the parser that is used to load this file. If unable to reload a project file, it is most likely due to the fact that the file names had some unusual characters (or spaces) in their paths that are breaking the parsing. For this reason, simple filenames and directories are recommended.

The Orthogonal Slice Viewer widget is used to view three, orthogonal, coordinate aligned 2D slices of the current volume. When activated, these three views will be displayed on the left side of the table surface. The orientations of these three views are locked to the local frame of the virtual objects, i.e. as the objects are rotated relative to the global world, the 2D slices remain the same. The current center point of the view window determines the 3D location of each of these three slices. This single point will always intersect all three of the slices. As the user navigates via the view window, the orthogonal slices update dynamically in response to the changing of this point. When active, the exact 3D locations of these slices will be shown in the World-In-Miniature as three separate frames. The following settings are available for this widget: (a) Show Slices (check box)—When checked, the slices are active and will displayed; (b) Mirror on Wall (check box)—If checked, and the slice viewer is active, the 2D slice views will be mirror on the vertical surface.

The Temporal FEA Loader widget is used to load in FEA data that follows the PLT format. This format lists the elements and their connectivity, followed by a series of time steps that contains the position of the vertices of all the elements and a number of data fields associated with these vertices. The file load window is used to browse to the location of a PLT file and after selected a set of time varying meshes is loaded from the file. After being loaded, the visual display of these meshes can be modified by changing the following settings: (a) Local Color Map (check box)—When checked, the mesh is colored such that the range of values is mapped to the maximum and minimum field values for the current time step. If off, a global color map is used where the range is defined by the field is determined across all time steps; (b) Flat Shading (check box)—If checked, when a PLT file is loaded the normals are computed using a flat shading local to each triangle instead of a smooth shading, useful if the mesh contains sharp edges; (c) Mesh Lighting On (check box)—When unchecked, the lighting is disabled for the current displayed FEA meshes; (d) Wireframe On (check box)—When checked, turns on a wireframe rendering for the current displayed FEA meshes; (e) Displayed Field (drop down)—Contains a list of all the fields that were loaded from the PLT file. After selected the displayed field is updated to reflect this field; (f) Color Map (drop down)—Contains a list of possible color mappings to use when rendering the displayed field. After selected the color of the field on the meshes is updated; (g) Skip Interval—It is possible that the set of all FEA meshes contained in the PLT file is too large to load into memory for the PC all at once. To be able to still load a representation of the entire dataset the skip interval can set and timesteps will be skipped to reduce the amount of data loaded.

The following section describes selected aspects of the program, according to one example.

Low-Level Strategies for Widgets/Controlling the 3D Touch System: One example allows for loading and simultaneously displaying multiple datasets. To realize the feature of supporting loading and simultaneously displaying multiple datasets (e.g., 3D surface, volumetric FEA data) notice that many widgets only affect one dataset at a time. This means that whenever a widget is activated it needs to be associated with the particular dataset upon which it should act. The function of loading and simultaneously displaying multiple datasets includes a new interface. To make the association between widget and dataset, the user drags the widget from the tool tray onto the shadow of the appropriate dataset. Then the widget activates at that position, right on top of the dataset's shadow. In one example, widgets that apply to all datasets (e.g., loading and saving an entire project, recording the screen to a movie file) are activated by dragging and dropping them anywhere on the table surface (and not necessarily on top of a dataset). In one example, widgets for loading a new dataset are activated by dragging them to a new position on the table, releasing, and then the new dataset will be loaded up at this location on the table. Similarly, in the camera path tool, the camera is associated with a particular 3D curve to fly along by dragging the camera widget onto the shadow of the 3D curve.

Centering a 3D Curve Relative to the Anatomy: In one example, a spline can be centered relative to selected anatomy. To support the feature of centering a spline (3D curve) that has been plotted inside the cavity of a 3D anatomy, an algorithm iterates through each control point of the spline, determines the distance from this point to the closest surface in all directions perpendicular to the spline, and then centers the control point based on these computed distances. In one example, an algorithm is configured to compute the average distance from the spline to the anatomy along the length of the spline.

Real-Time Interactive Iso-Surface Extraction: A significant amount of time is required in bringing new datasets into the tool. Some of this time is associated with using an external tool to extract an iso-surface from medical image stacks. One example of the present subject matter includes an iso-surface extractor widget which eliminates time spent on accessing an external tool. The widget is configured to perform a simple marching cubes iso value segmentation to extract the surface at a particular value. The value it uses is set by pointing the focus arrow at the display image slice on the table. The value immediately under the tip of the arrow is used as the iso value and a surface representing the boundary at that value is extracted. In the "Active Extract"

mode, the iso surface is continually extracted each time the widget is moved, making this a real-time interface for data exploration.

Generating a 3D Curve that Follows the Contour of Anatomy: One example includes a tool to map a cavity and contour of a 3D surface in an anatomical dataset. The tool executes an algorithm that uses an existing user-created spline to select an intersection point with the vertical surface. Three dimension rays are originated at this intersection point and radially projected outward to find the intersection with the anatomy. A new spline is created with these intersection points as the set of control points.

Three-Axis-Aligned Orthogonal 2D Viewplanes of Volume Data: One example includes a tool to support the visualization of the traditional three axial aligned (sagittal, coronal, transverse) views. The tool is configured to display three slices on the left hand side of the table surface. The 3D location of each of these slices is determined by a single point that intersects all three. This point is set by the user as they navigate using the Slice WIM metaphor and is determined by the 3D location of the bottom center of the view window (as indicated on the tabletop widget).

Anatomical Fly-Through with Device Radius Sizing: One example is configured to support camera fly-throughs relative to a set device size. This tool allows attachment of a camera widget to a user-created spline. After the camera widget is attached, the user can control the playback of the fly-though by pausing, reversing direction, and speeding up or slowing down the animation. The view is set during the fly-through by moving the WIM "through" according to the motion of the spline, in this way the view window remains fixated and the geometry moves through it, giving the effect of view motion. In addition, a user defined radius can be set that shows the size of a device as circle on the screen. The user can interpret the geometry relative to this device size to determine intersections and fit.

Figure 4N:
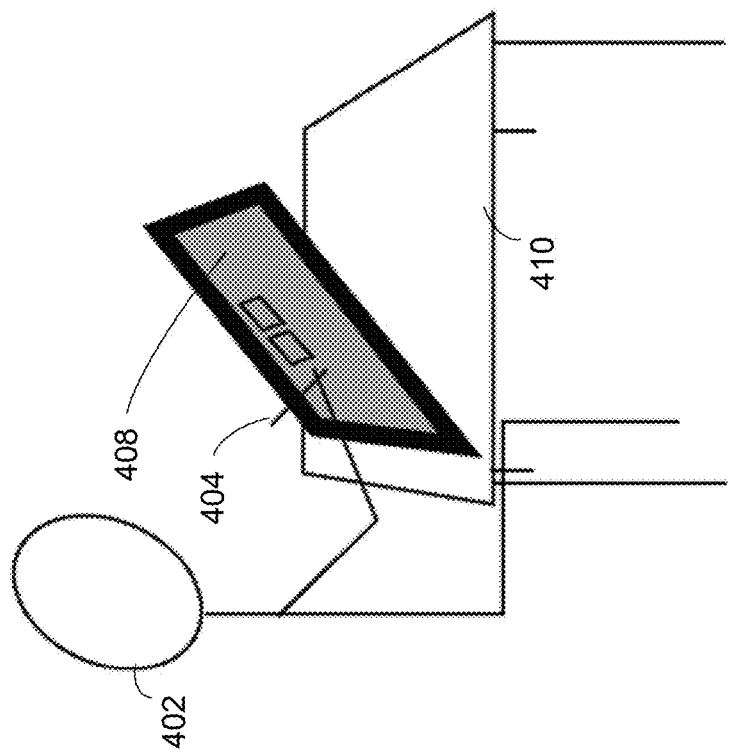
FIGS. 4M and 4N show a representation of a virtual desktop for manipulating and visualizing items such as anatomical items.
Figure 4M:
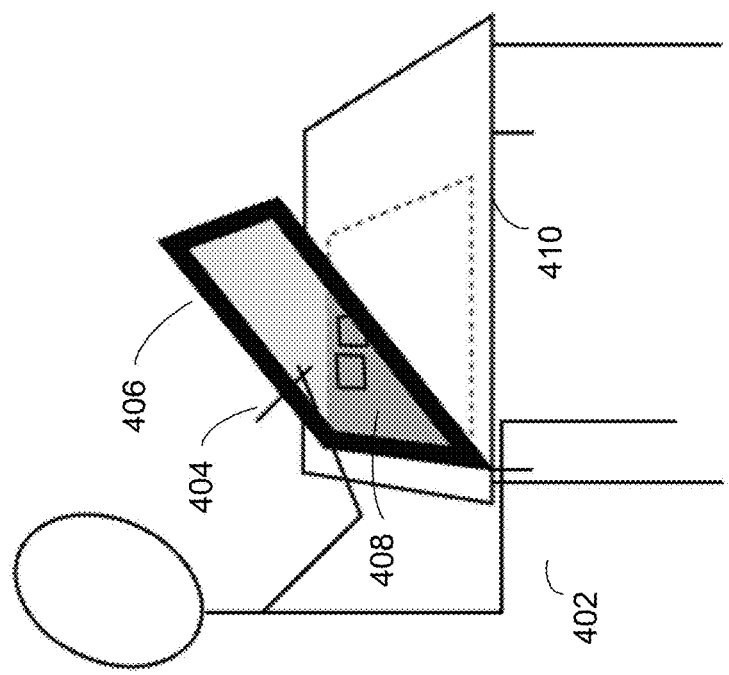

FIGS. 4M and 4N show a representation of a virtual desktop for manipulating and visualizing items such as anatomical items. In general, the representation shows features by which a user can manipulate a visual representation on an elevated desktop while other items such as icons are projected down into a virtual sub-desktop, an then have the items from the sub-desktop visually transitioned so that they can be interacted with more conveniently.

As shown in FIG. 4M, a human user 402 of a computer visualization system is seated at the system and is interacting with an elevated desktop 406 using a stylus 404. The elevated desktop 406 is implemented as a computer display, such as an LCD display that may be connected to hardware like that described above and below for the modeling and visualization of anatomical items. A "virtual table" 408 is drawn with 3D graphics so that it appears to lie in the plane of a real tabletop 410 lying beneath the elevated desktop that is sitting at an angle with respect to the horizontal real tabletop 410. When the virtual table 408 is in this horizontal position, it provides a visual grounding context for the 3D visualization on the virtual table 408. It also provides a 3D surface upon which the user 402 can view useful interaction widgets (buttons, color pickers, etc.). Such items may be visually behind the item being manipulated (e.g., a 3D model of a human heart that appears to user 402 as if it is floating in space at or about the plane of the elevated desktop 406. Therefore, the widgets can be presented without occluding any of the data visualization As shown in FIG. 4N, the virtual table has been automatically rotated upward through visual manipulation of the 3D presentation so that it now appears to be in the plane of the elevated desktop rather than in the plane of the real tabletop 410.

Such manipulation may be preferred when the widgets visually located on the real tabletop 410 become difficult to select for the user 402 because they appear several inches away from the physical display surface. Since the user 402 cannot reach out and directly touch these widgets, a "virtual laser pointer" technique is usually used to select such out-of-reach objects, but control of such a pointer can be challenging for some users. By allowing the user 402 to select a user-selectable displayed item, and in response, causing the display of the widgets and other menu items to visually rotate up from the lower displayed location to the higher location that is more directly correlated to the location the user 402 is touching, the interface may be easier for the user 402 to employ.

In one implementation of such a desktop system in use, a method may comprise: displaying on a slanted physical device positioned in a non-vertical and non-horizontal orientation, a three-dimensional model that appears to a user to be situated at or in front of the physical device; displaying on a first virtual surface visually behind the physical device a plurality of user-selected items that include icons, menus, or both; receiving a user input to change a displayed location of the user-selectable items; and in response to receiving the user input, transitioning the user-selectable items from the first virtual surface to be displayed as appearing to be on a surface of the slanted physical device. The first virtual surface may be a horizontal surface, such as a physical worktop on which the slanted physical device is resting. The first virtual surface may also be displayed behind the three-dimensional model so that when the three-dimensional model visually overlaps the first virtual surface, the three-dimensional model at least partially blocks display of the first virtual surface. The first virtual surface may also be displayed as a plane or as a curved surface. The displayed items may be user-selectable in a manner that changes a display of the three-dimensional model. The model may take the form of three-dimensional and four-dimensional models described above and below, and the user-interaction and processes described above and below may be employed with a desktop system like that described here.

FIGS. 5A and 5B show schematically a computation of distance from edges of an anatomical item to a 3D spline curve. Such steps reflected in the figures may be carried out automatically by a visualization system such as those discussed above and below so as to automatically place a spline in a most convenient physical location, such as to represent the center point of a path that a medical device, such as a stent, may be guided along through the anatomical item. The techniques described here can be used to determine the distance of an existing spline from the interior walls of an anatomical item like vasculature, or to locate a spline that is to be at a defined position relative to the internal wall, such as a spline that is to be centered on a length of vasculature.

FIG. 5A shows a point 506A on a spline at which measurements are to be made for determining distance to a wall 502 of a vessel or internal wall of a human heart. A computational method in this example identifies the point 506A as being a point along a spline curve, and generates a plurality of arrays around the spline at a orthogonal angle to the spline at that point of the spline. (Note that a second wall of the anatomical item is not shown, but would be located to the left of the spline.) The arrays may be generated at every n degrees around the spline, where n typically can be divided evenly into 360, such as every 10, 30, 60, or 120 degrees.

The spacing between the rays may also be uneven. The distance from point 506A to the wall of the anatomical item may be computed for each such array and stored. As shown by FIG. 5B, the measurement process may be repeated for a next point along a length of the spline, point 506B. In each instance, the arrays may draw out an internal outline of the shape of the anatomical item at the point, as 508A and 508B. The process may then be repeated for each of the identified points along the spline, where the points may be equally-spaced or unequally-spaced points along the spline.

In this manner, various computations and determinations may be made. For example, the cross sectional shape and area of the item can be determined, where the cross-section is roughly perpendicular to the passage at that point, rather than a horizontal slice through the item that may not adequately represent the geometry of the item. Such geometry may also be used to determine interaction between a medical device, which may subsequently located at each relevant point along the spline so as to model movement of the device through the anatomical item, and the tissue around the medical device at the relevant locations.

A spline may be automatically fit to a passage in a similar manner. As just one example, a user may identify a passage through which he would like a spline to be generated, such as a spline that closely follows the middle of the passage. A system may then step through a model of the item layer-by-layer, and compute a center of the opening (which for vasculature may be roughly a circle) at that layer, via standard techniques. Such a step may result in the creation of a plurality of points along a length of the passage, and a preliminary spline may be fit to those points. However, such a spline may not best track a centerline of the item if it curves along its length. As a result, the techniques just described may be applied to the preliminary spline, with the points that define the spline being adjusted in position until the rays are approximately equal in length around the spline. A final spline may then be generated from those points, which, rather than being simply equidistant from the walls of the item in a horizontal plane, are equidistant from the spline in a plane that is perpendicular to the axis of the spline at each relevant point along the spline.

Figure 6:
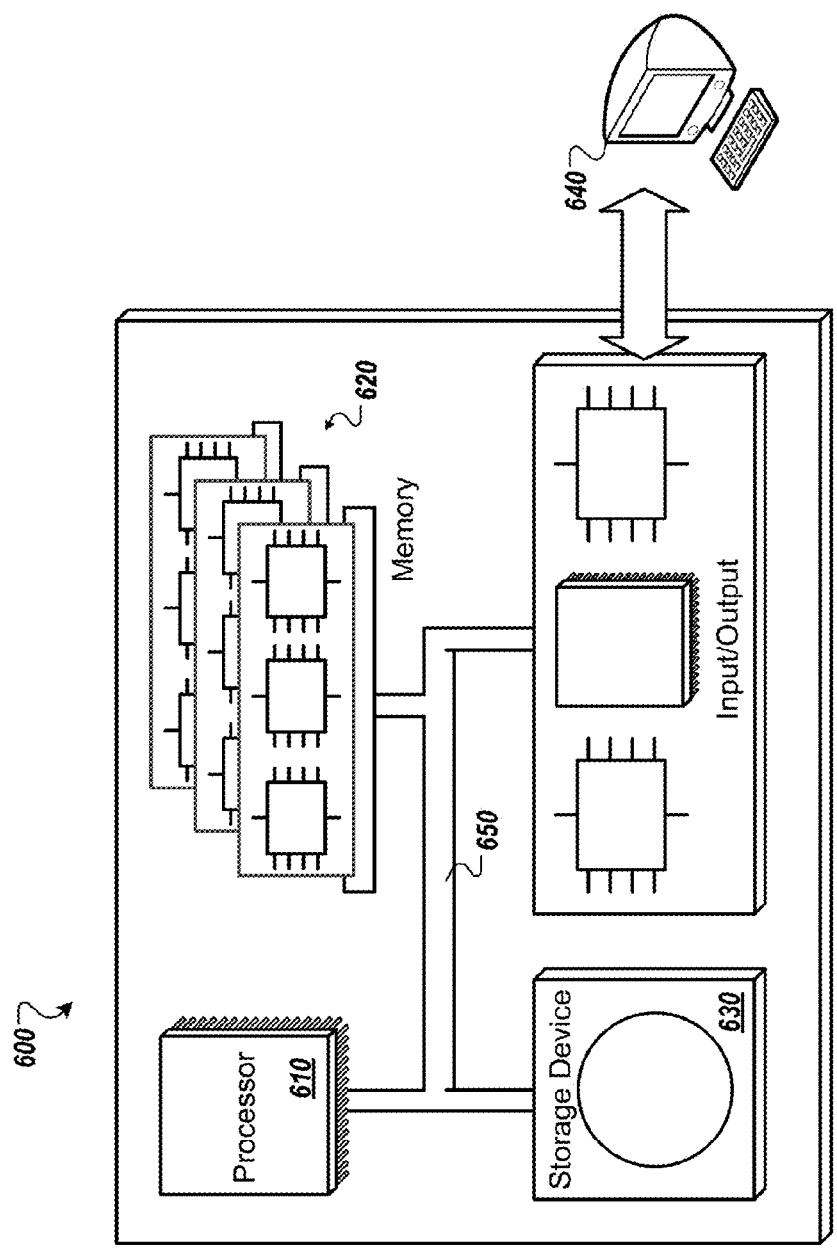
FIG. 6 shows an example of a computer device that can be used to implement the techniques described here.

FIG. 6 shows an example of a computer system that can be used to implement the techniques described here. The system 600 can be used for the operations described in association with any of the computer-implement methods described previously, according to one implementation. The system 600 is intended to include various forms of digital computers, such as laptops, desktops, workstations, personal digital assistants, servers, blade servers, mainframes, and other appropriate computers. The system 600 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 600 includes a processor 610, a memory 620, a storage device 630, and an input/output device 640. Each of the components 610, 620, 630, and 610, 620, 630, and 640 are interconnected using a system bus 650. The processor 610 is capable of processing instructions for execution within the system 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Other features may be implemented using the features discussed above, though they may not be part of the initially-filed claims. For example, A computer-implemented medical visualization method is disclosed that comprises identifying a three-dimensional model of an anatomical item of a particular mammal; identifying a force applied to tissue of the anatomical items; determining stress and strain on the tissue of the anatomical item using finite element analysis of the three-dimensional model; and displaying the anatomical item and a visual representation of strains determined for the tissue of the anatomical item as a result of the identified force. The anatomical item can comprise portions of a heart and the force applied on the anatomical item is identified based on movement of a virtual medical device through the heart. The virtual medical device can comprise a three-dimensional model that is modeled to have flexibility in at least one dimension. The method can also include automatically determining whether the virtual medical device makes contact with tissue in the three-dimensional model of the anatomical item as the virtual medical device is moved relative to the three-dimensional model of the heart. The method can additionally or alternatively include performing computational fluid dynamics analysis for fluid flowing around the medical device in the three-dimensional model of the heart.

In some aspects, the three-dimensional model of the anatomical item is generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid. The initial method may also comprise displaying an animation of the three-dimensional model of the anatomical item, the animation comprised of frames taken by imaging a real version of the anatomical item at different closely-related times, so as to show movement of the anatomical item. The method also may include showing differences in the anatomical item between particular ones of the frames computed by finite element analysis, and alternatively or additionally receiving an input from the user identifying locations in the three-dimensional model of the anatomical item, and displaying to the user distances in the model represented by the identified locations. Displaying the visual representation of strains determined for the tissue of the anatomical item as a result of the identified force can comprise displaying the anatomical item in different colors that each represent a particular level of strain.

In yet another implementations, a computer-implemented medical visualization method may be implemented and comprise: identifying a three-dimensional model of an anatomical item of a particular mammal; displaying a moving animation of the three-dimensional model, the moving animation created from multiple frames from imaging of the anatomical item over a sort time period to capture movement of the anatomical item; displaying one or more non-moving views of the three-dimensional model while the moving animation is being displayed; and in response to inputs from a user, changing the displayed moving animation and non or more non-moving views in coordination with each other. The method can also include displaying, in coordination between the moving animation and the one or more non-moving views, an device being moved through the anatomical item. The device can comprise a medical device, represented by a three-dimensional model, being moved through open passages in the anatomical item, and the anatomical item can comprise a heart. The method may additionally comprise displaying forces applied on the anatomical item based on movement of the device through the anatomical item. The displayed forces can be determined by applying finite element analysis to a tissue model for the anatomical item. Also, the initial process may comprise automatically determining whether the medical device makes contact with tissue in anatomical item as the medical device is moved relative to the three-dimensional model of the anatomical item. The method can additionally include performing computational fluid dynamics analysis for fluid flowing around the medical device in the anatomical item, and displaying to the user information representing results of the computational fluid dynamics analysis.

In certain aspects, the three-dimensional model of the anatomical item is generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid. Also, the moving animation can be comprised of frames taken by imaging a real version of the anatomical item at different closely-related times, so as to show movement of the anatomical item. In addition, a first non-moving view shows the anatomical item during a first imaging session, and a second non-moving view shows the anatomical item during a second imaging session. Moreover, the first imaging session can be a pre-operative imaging session, and the second imaging session can be a post-operative imaging session.

In another implementation, a computer-implemented medical visualization method is disclosed that comprises identifying first and second three-dimensional models of an anatomical item of a particular mammal, wherein the first model is formed from imaging data taken at a first imaging session, and the second model is formed from imaging data taken at a separate, second imaging session; displaying the first model on a computer-generated visual display; and displaying the second model on the computer-generated visual display concurrently with displaying the first model. The method can also comprise receiving a user input to manipulate one of the first or second model, or both, and changing a view of the first model and a view of the second model in coordination with each other responsive to the received user input. The first three-dimensional model can represent an anatomical item pre-operation, and the second three-dimensional model can represent the anatomical item post-operation. The anatomical item can comprise a heart or other organ.

In some aspects, the method further comprises displaying the first and second three-dimensional models as animations showing motion of the anatomical item, wherein the animations are displayed in time-wise coordination with each other. The animations can be displayed as repeating, looping animations, and views of the models that are displayed change in response to user input. The method can also include displaying forces applied on the anatomical item based on movement of a virtual device through the one or more of the models of the anatomical item. In some aspects, the three-dimensional model of the anatomical item is generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid.

In yet another implementation, a computer-implemented medical visualization method is disclosed that comprises identifying a three-dimensional model of an anatomical item of a particular mammal; displaying a view of the three-dimensional model on a computer-based visualization system; receiving input from a user identifying at least two points on the displayed view of the three-dimensional model; and providing to the user data that indicates a measurement based on the identified at least two points, the measurement representing a scale on the anatomical item. The method can also comprise selecting a device sized according to the measurement, and displaying the device in the anatomical item. Displaying the device in the anatomical item can comprise moving the device along a path defined in open passages of the three-dimensional model. Also, the device can comprise a medical device, represented by a three-dimensional model, being moved through open passages in the anatomical item, and the anatomical item can comprise a heart or other animal (e.g., human) organ. The method can also include displaying forces applied on the anatomical item based on movement of the device through the anatomical item, and the displayed forces can be determined by applying finite element analysis to a tissue model for the anatomical item. Moreover, the method can include displaying a moving animation of the three-dimensional model and presenting to the user changing measurements as the animation moves.

In some aspects, the measurement represents a radius, diameter, area, or volume of an open space in the anatomical item. Also, the three-dimensional model of the anatomical item can be generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid.

In another implementation, a computer-implemented medical visualization method is disclosed that comprises identifying first data representing an anatomical item of a particular mammal, the first data obtained by a first type of medical imaging; identifying second data representing the anatomical item, the second data obtained by a second type of medical imaging that is different from the first type of medical imaging; and building a three-dimensional solid model of the anatomical item using a combination of the first data and the second data. The first data can represent slices of the anatomical item at multiple different elevations, and the second data can represent slides of the anatomical item at multiple different elevations. Moreover, the first data and the second data can represent slices that are determined to be essentially parallel to each other. The first type of medical imaging can comprise magnetic resonance imaging, and the second type of medical imaging can comprise computer tomography imaging. The method may also include displaying, in coordination, a moving animation of the anatomical item generated from the three-dimensional solid model and a non-moving view of the anatomical item generated from the three-dimensional solid model, and change views of the animation and the non-moving view based on user inputs received by a computer visualization system. The anatomical item can comprise a heart or other organ. The method can also comprise displaying forces applied on the anatomical item based on movement of a device through the three-dimensional model. Also, the displayed forces can be determined by applying finite element analysis to a tissue model for the anatomical item.

In some aspects, the three-dimensional model of the anatomical item is generated by operations comprising: obtaining data that represents imaged two-dimensional slices of the anatomical item captured by the first and second types of medical imaging; generating a three-dimensional mesh from points identified in the two-dimensional slices;

and generating the three-dimensional model from the three-dimensional grid. The method can also include building a second three-dimensional model of the anatomical item using data captured in separate sessions of the first type of medical imaging and the second type of medical imaging, wherein the separate sessions are different than sessions used to generate data for the initial three-dimensional model.

In another implementation, a computer-implemented medical visualization method, is disclosed that comprises identifying a three-dimensional model of an anatomical item of a particular mammal; displaying the three-dimensional model on a computer-based visualization system; receiving input from a user to add items in positional relationship with the three-dimensional model; and storing meta data defining the added items in association with the three-dimensional model so that the added items can be automatically displayed with the three-dimensional model when the three-dimensional model is accessed in the future. The three-dimensional model of the anatomical item is generated by operations can comprise: obtaining data that represents imaged two-dimensional slices of the anatomical item captured by one or more medical imaging systems; generating a three-dimensional mesh from points identified in the two-dimensional slices; and generating the three-dimensional model from the three-dimensional grid.

In another implementation, a computer-implemented medical visualization method comprises identifying a three-dimensional model of an anatomical item of a particular mammal; displaying the three-dimensional model on a computer-based visualization system; receiving input from a user defining multiple non-parallel cutting planes; and displaying the three-dimensional model with portions of the three-dimensional model removed as defined by the multiple non-parallel cutting planes. The multiple non-parallel cutting planes can define a corner of a box that is overlaid with a portion of the three-dimensional model so as to cut a corner visually into the three-dimensional model. The anatomical item can comprise a heart, and the three-dimensional model of the anatomical item can be generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid.

In yet another implementation, a computer-implemented medical visualization method is disclosed that comprises identifying a three-dimensional model of an anatomical item of a particular mammal; identifying different sub-portions of the three-dimensional model based on physiological roles placed by the different sub-portions; displaying the three-dimensional model on a computer-based visualization system; and presenting user-selectable controls for manipulating the three-dimensional model on the basis of the identified different sub-portions. The different sub-portions are assigned to defined layers of the three-dimensional model that can be separately activated, colored with a defined color, or both. The anatomical item can comprise a heart, and the three-dimensional model of the anatomical item can be generated by operations comprising: obtaining data that represents imaged two-dimensional slices of the anatomical item captured by one or more medical imaging systems; generating a three-dimensional mesh from points identified in the two-dimensional slices; and generating the three-dimensional model from the three-dimensional grid.

In another implementation, a computer-implemented medical visualization method is disclosed that comprises identifying a three-dimensional model of an anatomical item of a particular mammal; displaying the three-dimensional model on a computer-based visualization system of a user who is viewing the actual anatomical item; and changing the display of the three-dimensional model automatically in response to interaction by the user with the actual anatomical item. The computer-based visualization system can comprises electronic glasses worn by the user, and the interaction by the user can comprise inserting a medical device into the particular mammal, and changing the display comprises showing a representation of progress of the device advancing internal to the anatomical item. The anatomical item can comprise a portion of a circulatory system, and progress of the device can comprise progress of advancing an implantable cardiac device at a location in the circulatory system. The anatomical item can comprise a heart or other organ, or a portion of vasculature.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for medical device modeling, comprising:
   accessing an electronic definition for a model of a three-dimensional item, an electronic definition of a three-dimensional anatomical item having an internal anatomical volume, and an electronic definition of a three-dimensional spline relating to the internal anatomical volume;
   determining, with a computer-based finite element analysis system and using the electronic definitions, stresses created by the three-dimensional item on the anatomical item for a plurality of locations of the three-dimensional item along the three-dimensional spline, including at a first location of the three-dimensional item along the three-dimensional spline and at a second location of the three-dimensional item along the three-dimensional spline;
   moving the three-dimensional item along the three-dimensional spline, and visually representing the three-dimensional item as it is moved along the three-dimensional spline; and
   displaying stress data generated by the finite element analysis system with a visualization system, the display of the stress data indicating levels of stress on portions of the three-dimensional item and levels of stress on portions of the anatomical item at particular locations along the three-dimensional spline.

2. The computer-implemented method of claim 1, wherein the three-dimensional item comprises a model of a medical device.

3. The computer-implemented method of claim 2, wherein the medical device comprises a stent, and the model is formed as a cylinder having a longitudinal axis that is aligned with an axis of the three-dimensional spline curve.

4. The computer-implemented method of claim 1, wherein the one or more stresses are determined by a finite element solver that is external to the visualization system.

5. The computer-implemented method of claim 4, wherein the finite element solver is at a site that is separate from a site that houses the visualization system, and the finite element solver serves a plurality of different visualization systems at different sites, and communicates with the visualization systems over a network-based connection.

6. The method of claim 4, further comprising displaying multiple stress visualizations and corresponding anatomical models side-by-side with each other for visual comparison.

7. The method of claim 1, where the stresses are automatically determined repeatedly for different splines having different shapes in one or more anatomical models.

8. The method of claim 1, further comprising determining, using computational fluid dynamics techniques, information describing flow characteristics for fluid flowing through the internal anatomical volume.

9. The method of claim 8, wherein the information describing flow characteristics is generated by determining fluid flow around the three-dimensional item.

10. The method of claim 1, further comprising identifying electrical characteristics for tissue surrounding the internal anatomical volume, and determining the stresses as a function of the electrical characteristics.

11. The method of claim 10, wherein the electrical characteristics comprise electrical charge propagating over time through heart tissue as part of a cardiac cycle.

12. The method of claim 10, wherein the electrical characteristics are used to determine muscle contraction of a heart and the stresses are determined as a function of the forces exerted on and by the heart tissue.

13. The method of claim 1, further comprising, for each particular point of a plurality of points along a path through the internal anatomical volume, automatically performing operations comprising:
generating a plurality of rays around the particular point in a common plane; and
determining lengths of each of the plurality of rays from the particular point to a boundary of the internal anatomical volume.

14. The method of claim 1, wherein the internal anatomical volume is defined by a model of an anatomical item generated by operations comprising:
obtaining data that represents imaged two-dimensional slices of the anatomical item captured by one or more medical imaging systems;
generating an intermediate three-dimensional representation from points identified in the two-dimensional slices; and
generating the three-dimensional model from the intermediate three-dimensional representation.

15. The method of claim 1, further comprising:
determining stresses on the three-dimensional item created by forces from the motion of a heart; and
using the determined forces to display the levels of stress on the portions of the three-dimensional item.

16. The method of claim 1, wherein the stress data is displayed as a four-dimensional model in which the three-dimensional item moves along the three-dimensional spline.

17. One or more machine-readable, non-transitory devices storing instructions that, when executed by one or more computer processors, perform operations comprising:
accessing an electronic definition for a model of a three-dimensional item, an electronic definition of a three-dimensional anatomical item having an internal anatomical volume, and an electronic definition of a three-dimensional spline relating to the internal anatomical volume;
determining, with a computer-based finite element analysis system and using the electronic definitions, stresses created from passing the three-dimensional item along the three-dimensional spline, for a plurality of locations of the three-dimensional item along the three-dimensional spline, including at a first location of the three-dimensional item along the three-dimensional spline and at a second location of the three-dimensional item along the three-dimensional spline;
moving the three-dimensional item along the three-dimensional spline, and visually representing the three-dimensional item as it is moved along the three-dimensional spline; and
displaying stress data generated by the finite element analysis system with a visualization system, the display of the stress data indicating levels of stress on portions of the three-dimensional item and levels of stress on portions of the anatomical item at particular locations along the three-dimensional spline.

18. The one or more devices of claim 17, wherein the three-dimensional item comprises a model of a medical device.

19. The one or more devices of claim 18, wherein the medical device comprises a stent, and the model is formed as a cylinder having a longitudinal axis that is aligned with an axis of the three-dimensional spline curve.

20. The one or more devices of claim 18, further comprising identifying electrical characteristics for tissue surrounding the internal anatomical volume, and determining the stresses as a function of the electrical characteristics.

21. The one or more devices of claim 17, wherein the one or more stresses are determined by a finite element solver that is external to the visualization system.

22. The one or more devices of claim 21, wherein the finite element solver is at a site that is separate from a site that houses the visualization system, and the finite element solver serves a plurality of different visualization systems at different sites, and communicates with the visualization systems over a network-based connection.

23. The one or more devices of claim 17, further comprising determining, using computational fluid dynamics techniques, information describing flow characteristics for fluid flowing through the internal anatomical volume.

24. The one or more devices of claim 17, wherein the internal anatomical volume is defined by a model of an anatomical item generated by operations comprising:
obtaining data that represents imaged two-dimensional slices of the anatomical item captured by one or more medical imaging systems;
generating an intermediate three-dimensional representation from points identified in the two-dimensional slices; and
generating the three-dimensional model from the intermediate three-dimensional representation.

25. A computer-implemented method for medical device modeling, comprising:
accessing an electronic definition for a model of a three-dimensional item, an electronic definition for a dynamic model of motion forces generated by a heart, and an electronic definition of a three-dimensional spline relating to an anatomical item having an internal anatomical volume;
determining, with a computer-based finite element analysis system and using the electronic definitions, stresses created by the three-dimensional item along the three-dimensional spline;
moving the three-dimensional item along the three-dimensional spline, and visually representing the three-dimensional item as it is moved along the three-dimensional spline; and displaying stress data generated by the finite element analysis system with a visualization system, the display of the stress data indicating levels of stress on portions of the anatomical item at particular locations along the three-dimensional spline.

* * * * *